United States Patent
Solitario, Jr.

(10) Patent No.: US 8,641,720 B2
(45) Date of Patent: Feb. 4, 2014

(54) ORTHOPEDIC IMPLANT SYSTEM

(75) Inventor: Ralph C. Solitario, Jr., West Chester, PA (US)

(73) Assignee: DePuy Synthes Products, LLC, Raynham, MA (US)

( * ) Notice: Subject to any disclaimer, the term of this patent is extended or adjusted under 35 U.S.C. 154(b) by 146 days.

(21) Appl. No.: 13/195,962

(22) Filed: Aug. 2, 2011

(65) Prior Publication Data

US 2012/0029580 A1 Feb. 2, 2012

Related U.S. Application Data

(60) Provisional application No. 61/369,884, filed on Aug. 2, 2010.

(51) Int. Cl.
*A61B 17/70* (2006.01)

(52) U.S. Cl.
USPC .......................................... 606/86 A; 606/104

(58) Field of Classification Search
USPC ........................... 606/86 A, 914, 916, 104, 99
See application file for complete search history.

(56) References Cited

U.S. PATENT DOCUMENTS

| | | | | |
|---|---|---|---|---|
| 8,192,438 | B2* | 6/2012 | Garamszegi | 606/86 A |
| 2001/0047173 | A1 | 11/2001 | Schlapfer | |
| 2003/0199872 | A1* | 10/2003 | Markworth et al. | 606/61 |
| 2005/0049588 | A1 | 3/2005 | Jackson | |
| 2005/0090824 | A1* | 4/2005 | Shluzas et al. | 606/61 |
| 2006/0106380 | A1* | 5/2006 | Colleran et al. | 606/61 |
| 2006/0247630 | A1* | 11/2006 | Iott et al. | 606/61 |
| 2006/0264962 | A1 | 11/2006 | Chin et al. | |
| 2006/0293659 | A1 | 12/2006 | Alvarez | |
| 2007/0016200 | A1 | 1/2007 | Jackson | |
| 2007/0078460 | A1* | 4/2007 | Frigg et al. | 606/61 |
| 2007/0270842 | A1 | 11/2007 | Bankoski et al. | |
| 2008/0077136 | A1* | 3/2008 | Triplett et al. | 606/61 |
| 2008/0077138 | A1 | 3/2008 | Cohen et al. | |
| 2009/0105774 | A1* | 4/2009 | Jones et al. | 606/86 A |
| 2010/0036443 | A1 | 2/2010 | Hutton et al. | |

FOREIGN PATENT DOCUMENTS

| | | |
|---|---|---|
| WO | WO 2006/116437 | 11/2006 |
| WO | WO 2007/038350 | 4/2007 |
| WO | WO 2009/015100 | 1/2009 |

* cited by examiner

*Primary Examiner* — Jan Christopher Merene
(74) *Attorney, Agent, or Firm* — Woodcock Washburn LLP

(57) ABSTRACT

A surgical instrument is configured to introduce a spinal fixation rod into a vertebral implant such that once the spinal fixation rod is engaged with the surgical instrument and the surgical instrument is put into a retention configuration, the spinal fixation rod cannot be removed from the surgical instrument until the spinal fixation rod is properly located and oriented with respect to the surgical construct and the surgical instrument is released from the retention configuration. The surgical instrument for introducing a spinal fixation rod includes a surgical instrument body with an actuator, and an engagement assembly at opposing ends and a transfer assembly extending between the actuator and the engagement assembly. The surgical instrument can also be used as part of a method for introducing a spinal fixation rod. Additionally, the surgical instrument can be part of a kit for introducing a spinal fixation rod, the kit including a plurality of spinal fixation rods of varying shapes and sizes.

28 Claims, 19 Drawing Sheets

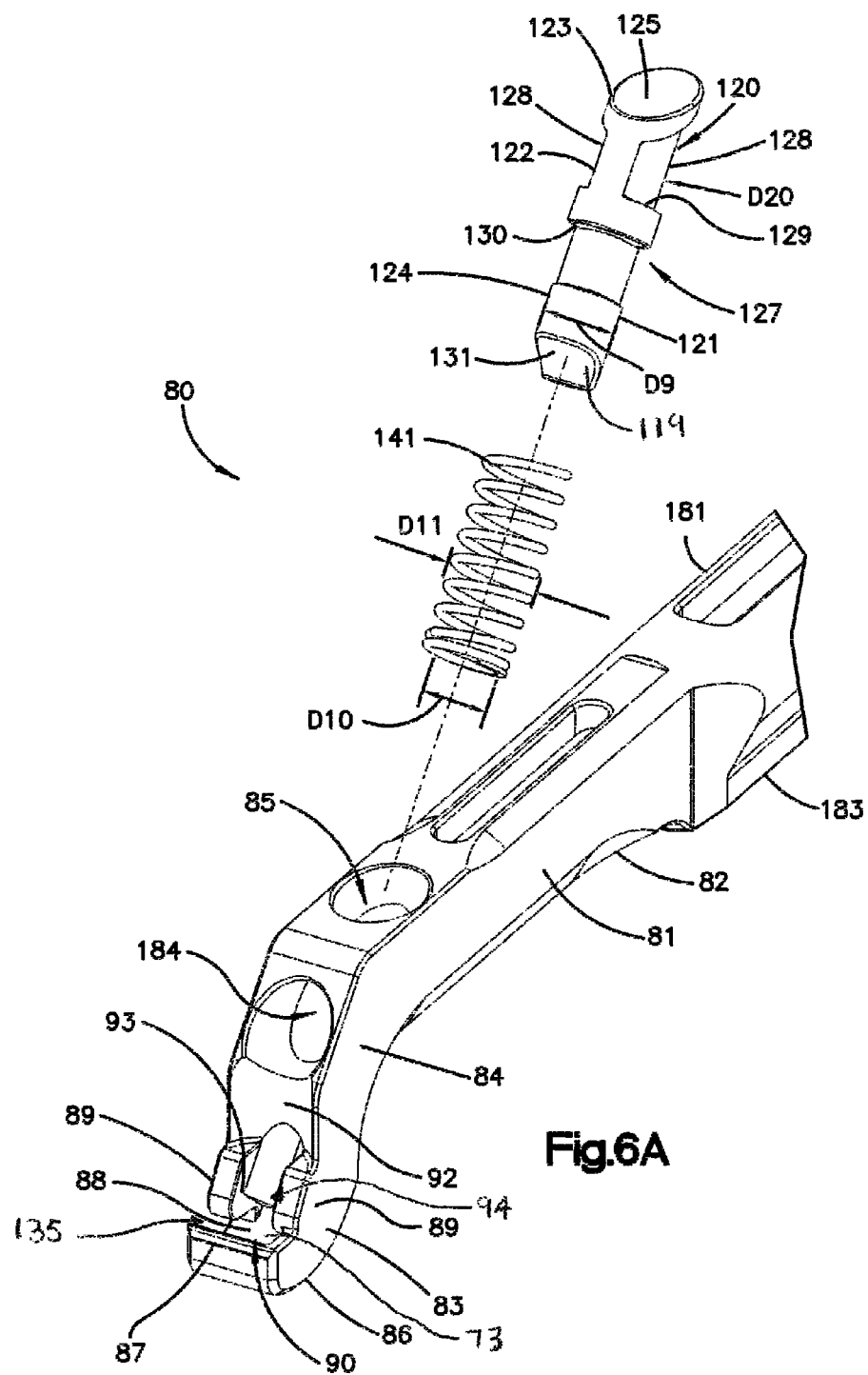

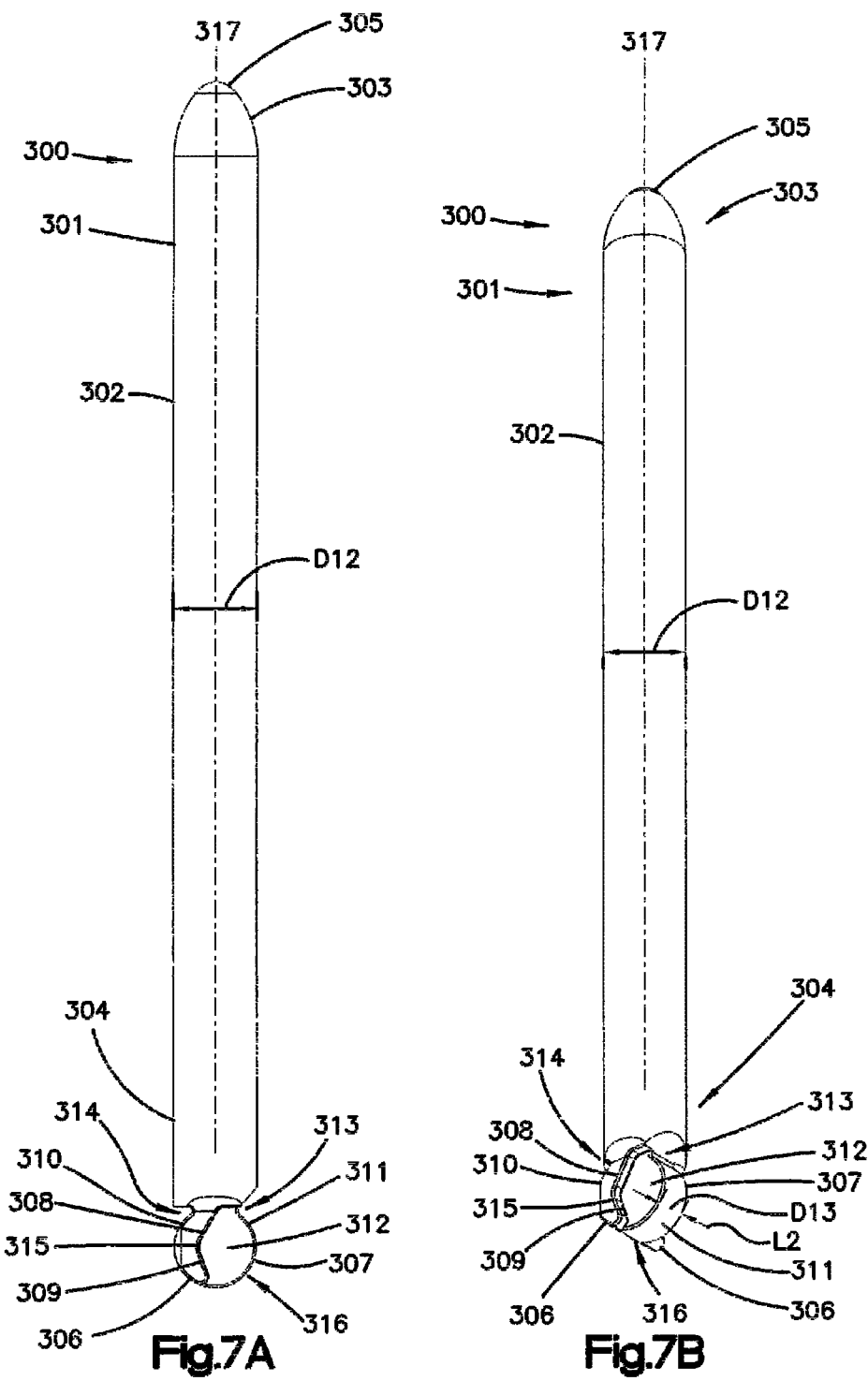

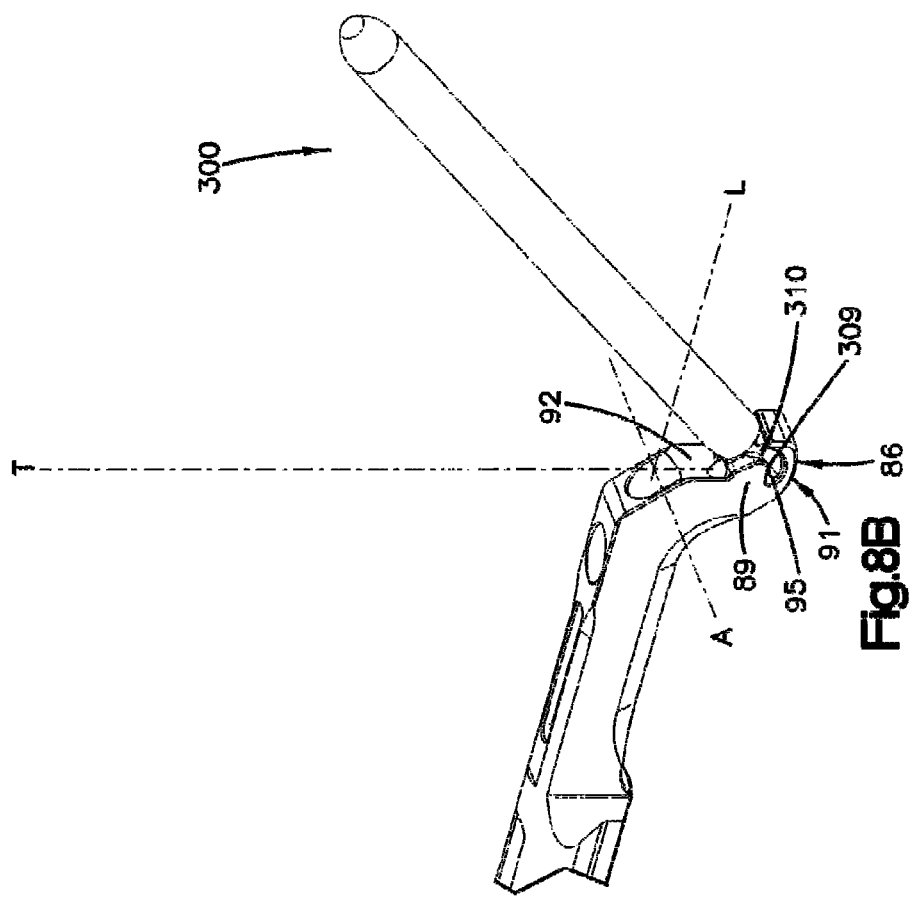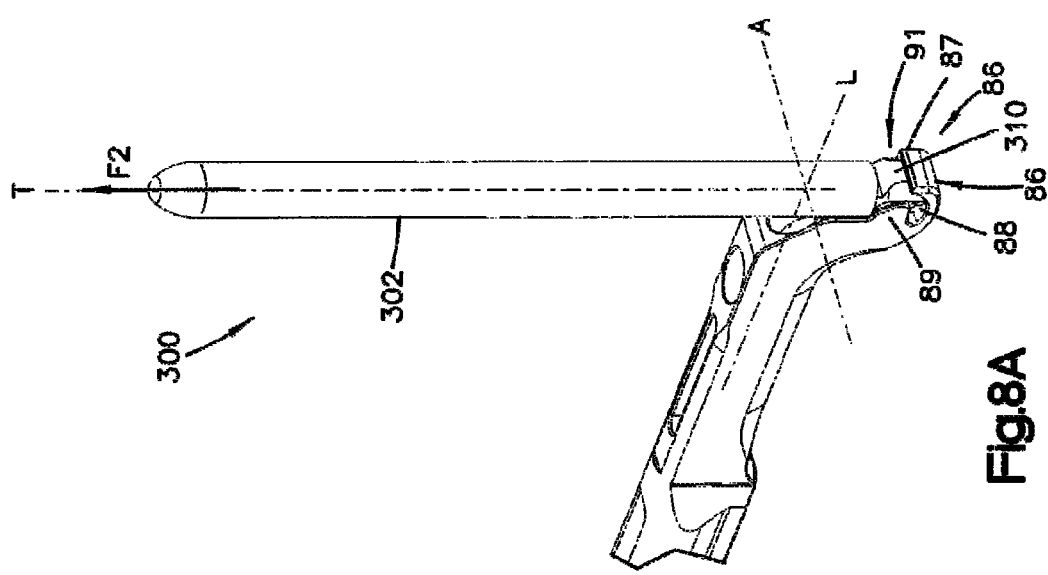

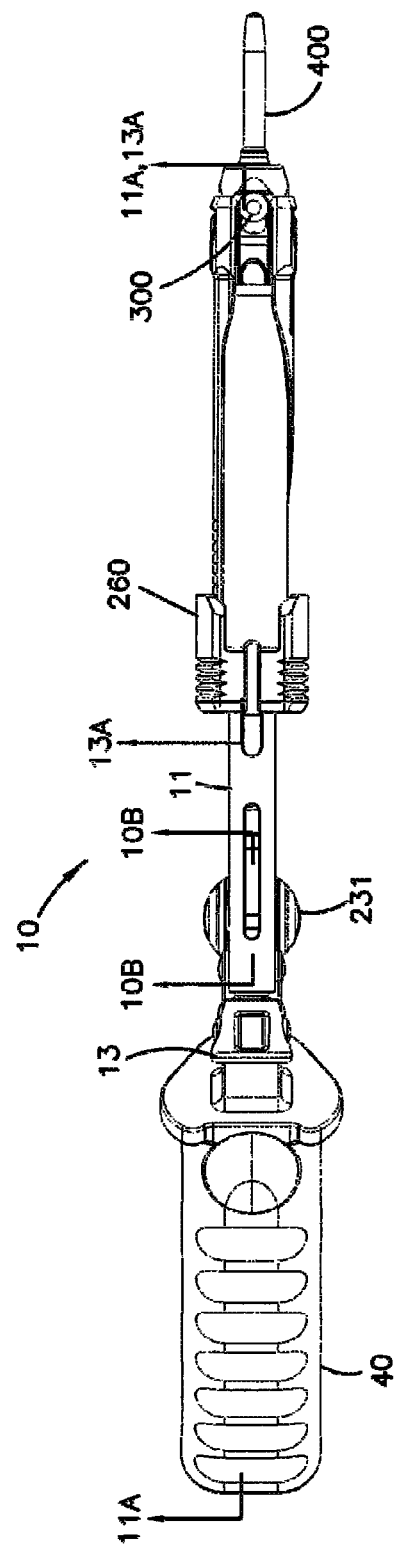

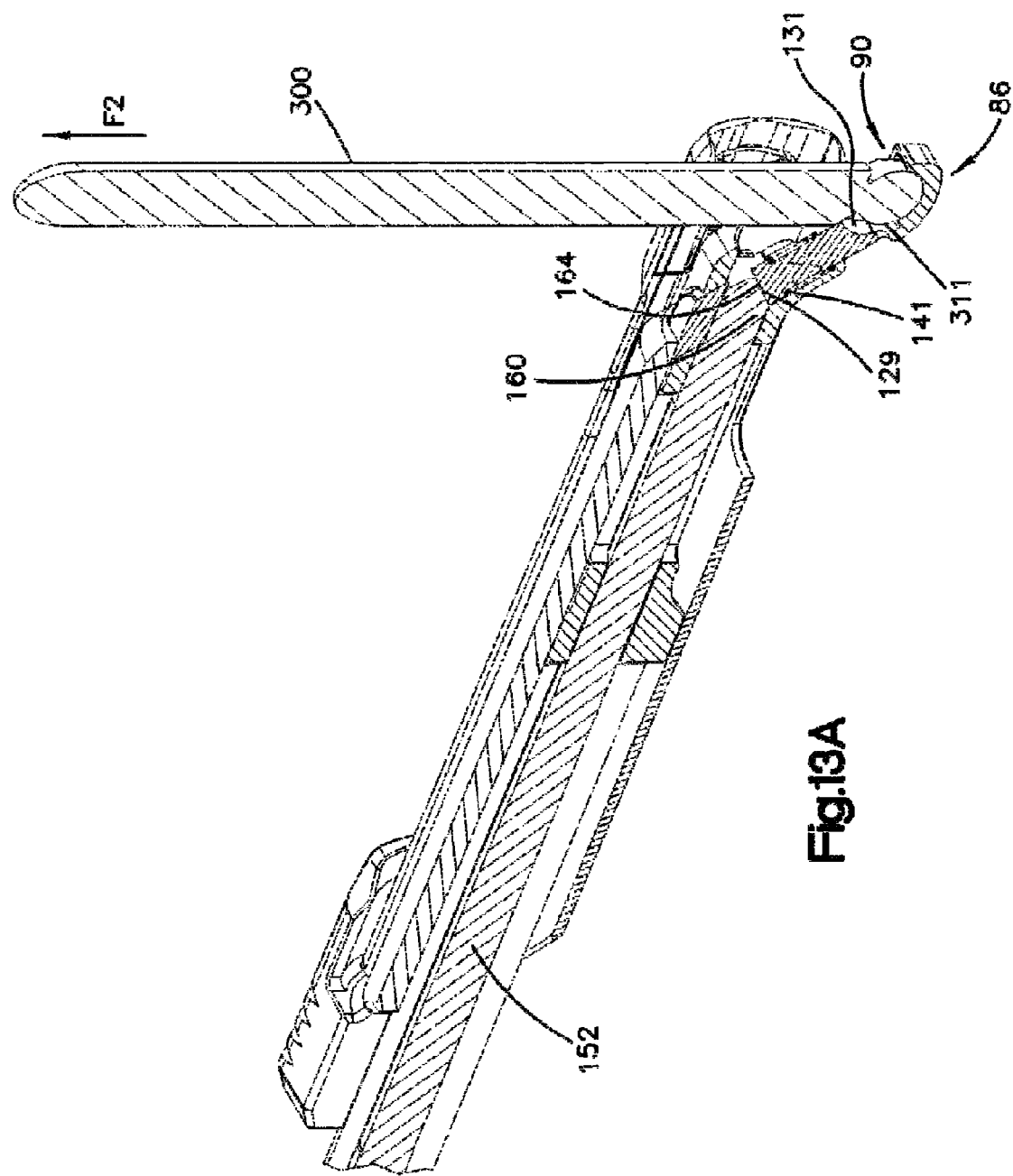

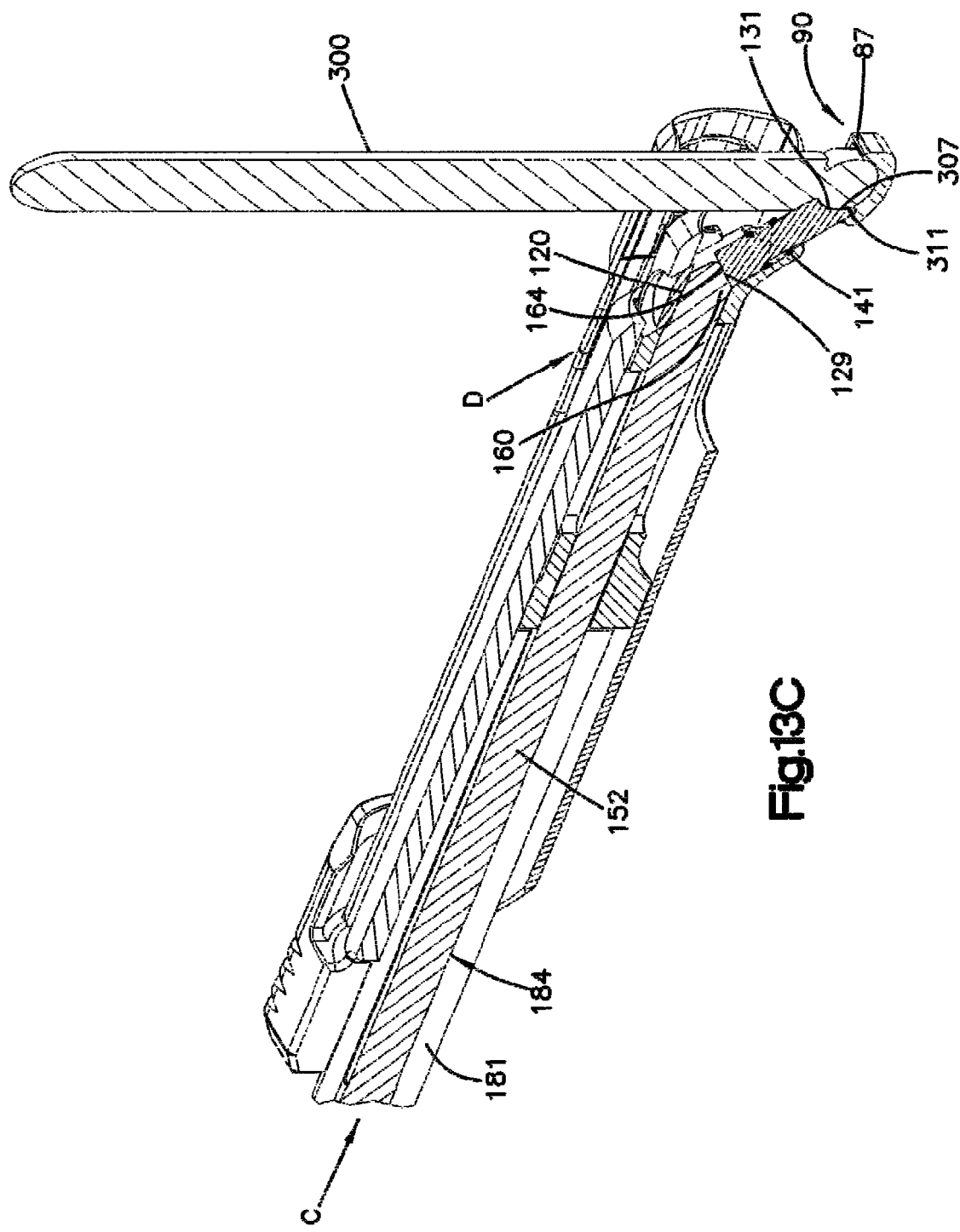

ORTHOPEDIC IMPLANT SYSTEM

CROSS-REFERENCE TO RELATED APPLICATIONS

This application claims priority, and the benefit of, U.S. Provisional Application No. 61/369,884 filed on Aug. 2, 2010, the contents of which are hereby incorporated by reference in their entirety.

TECHNICAL FIELD

The present disclosure relates generally to orthopedics, and in particular relates to an implant system configured to implant a spinal fixation rod.

BACKGROUND

Spinal fusion is a surgical procedure used to join two or more vertebrae. The procedure is primarily used to eliminate pain, which can be caused by a number of conditions, such as degenerative disc disease, vertebral fracture, spondylolisthesis and other diseases that cause instability of the spine.

In most spinal fusion procedures, spinal fixation rods are attached to vertebral implants, which are first secured to adjacent vertebrae. The vertebral implants generally include a bone anchor seat, a collet disposed inside the anchor seat, and a bone anchor with a head portion attached to the collet. The spinal fixation rod is inserted through the collet and fixed in place by a locking cap that attaches to the collet.

The placement of a spinal fixation rod within a vertebral implant typically required a large opening in a patient's body to provide a surgeon with the visibility required at the surgical site. Recently, minimally invasive surgeries have become more common and desirable as they reduce complications during surgery and recovery time after surgery. Minimally invasive spinal fusion surgery presents a number of unique challenges including: retention of the spinal fixation rod within the surgical instrument during the insertion process; manipulation of the spinal fixation rod while it is inside the patient; and proper alignment and positioning of the spinal fixation rod relative to the vertebral implants.

SUMMARY

In accordance with one embodiment, a surgical instrument is configured to introduce a spinal fixation rod into, for instance, a series of pedicle screws. The surgical instrument includes a gripping portion, a housing member attached to the gripping member and defining an inner bore, a shaft positioned within the inner bore, an engagement tip attached to the housing member opposite the gripping portion and defining a second inner bore, and an inner core positioned within the second inner bore.

In accordance with another embodiment, a surgical kit includes a surgical instrument configured to introduce a spinal fixation rod, and a plurality of spinal fixation rods. The fixation rods can have different sizes and shapes.

In accordance with one embodiment, a surgical instrument includes an engagement assembly, a transfer assembly, and an actuator. The engagement assembly includes a motion inhibitor configured to releasably engage the spinal fixation rod and an engagement pocket defining a rod receiving gap configured and sized to receive a portion of a spinal fixation rod and to permit the spinal fixation rod to pivot therein. The transfer assembly includes a shaft operably coupled to the motion inhibitor. The actuator is operably coupled to the shaft so as to translate the shaft upon actuation of the actuator. The movement of the shaft causes at least one of the first and second engagement walls to move toward the other of the first and second engagement walls between a first position in which the rod receiving gap has a first size and a second position in which the rod receiving gap has a second size. The second size is less than the first size.

In one embodiment, the motion inhibitor is movable upon translation of the shaft to a third position in which the rod receiving gap has a third size, the third size being less than the second size.

In yet another embodiment, the engagement pocket includes a lip, a curved lower surface extending from lip, and laterally opposed first and second retaining walls spaced apart from each other. Each of the first and second retaining walls includes a bottom surface that is separated from the lower surface so as to define a retention gap therebetween. The retention gap is shaped and sized to receive a pair of engagement rails disposed on opposite sides of the end portion of the spinal fixation rod of the spinal fixation rod. The motion inhibitor includes the second engagement wall at a distal end thereof.

In one embodiment, the engagement assembly defines an ejection port in communication with the rod receiving gap. The ejection port faces a direction substantially perpendicular to a longitudinal axis defined along a length of the surgical instrument. The engagement assembly includes at least one retaining wall and a lip extending substantially perpendicular to the longitudinal axis defined along the length of the surgical instrument at the ejection port. The engagement assembly includes at least one retaining wall and a lip extending substantially perpendicular to the longitudinal axis defined along the length of the surgical instrument at the ejection port. The engagement pocket is contoured and sized to allow removal of the spinal fixation rod therefrom only when the spinal fixation rod is substantially perpendicular to the longitudinal axis defined by the surgical instrument body and when the motion inhibitor is in the first position. The motion inhibitor includes an auxiliary shaft having first and second ends. The auxiliary shaft includes a curved brake surface at the second end thereof. The curved brake surface is configured to contact the spinal fixation rod. The curved brake surface has a substantially concave configuration. The curved brake surface of the motion inhibitor is configured to receive a curve brake surface of the spinal fixation rod. The surgical instrument further includes a surgical instrument body defining a longitudinal axis and connected to the actuator and the engagement assembly. The surgical instrument body defines an inner bore extending along the longitudinal axis. The inner bore being is and dimensioned to slidably receive the shaft. The engagement assembly defines a transverse bore configured and dimensioned to slidably receive the motion inhibitor. The transverse bore is in communication with the inner bore and the engagement pocket. The engagement assembly further includes a biasing member disposed within the transverse bore and surrounding the motion inhibitor. The biasing member is configured to bias the motion inhibitor away from the engagement pocket. The engagement pocket further includes a lip that acts as stop, limiting the pivotal motion of the spinal fixation rod disposed in the engagement pocket.

In another embodiment, a system for implanting a spinal fixation rod generally includes a spinal fixation rod and surgical instrument. The surgical instrument includes an engagement assembly, a transfer assembly, and an actuator. The engagement assembly includes a motion inhibitor configured to releasably engage the spinal fixation rod and an engagement pocket defining a rod receiving gap configured and sized to receive a portion of a spinal fixation rod and to permit the spinal fixation rod to pivot therein. The transfer assembly includes a shaft operably coupled to the motion inhibitor. The actuator is operably coupled to the shaft so as to translate the shaft upon actuation of the actuator. The movement of the shaft causes at least one of the first and second engagement walls to move toward the other of the first and second engagement walls between a first position in which the rod receiving gap has a first size and a second position in which the rod receiving gap has a second size. The second size is less than the first size.

In one embodiment, the motion inhibitor is movable upon translation of the shaft to a third position in which the rod receiving gap has a third size, the third size being less than the second size. The engagement assembly defines an ejection port in communication with the rod receiving gap. The ejection port faces a direction substantially perpendicular to a longitudinal axis defined along a length of the surgical instrument. The engagement pocket is contoured and sized to allow removal of the spinal fixation rod therefrom only when the spinal fixation rod is substantially perpendicular to the longitudinal axis defined by the surgical instrument body and when the motion inhibitor is in the first position. The motion inhibitor includes an auxiliary shaft having first and second ends. The auxiliary shaft includes a curved brake surface at the second end thereof. The curved brake surface is configured to contact the spinal fixation rod. The curved brake surface has a substantially concave configuration. The curved brake surface of the motion inhibitor is configured to receive a curve brake surface of the spinal fixation rod. The surgical instrument further includes a surgical instrument body defining a longitudinal axis and connected to the actuator and the engagement assembly. The motion inhibitor includes the second engagement wall at a distal end thereof. The surgical instrument body defines an inner bore extending along the longitudinal axis. The inner bore being is and dimensioned to slidably receive the shaft. The engagement assembly defines a transverse bore configured and dimensioned to slidably receive the motion inhibitor. The transverse bore is in communication with the inner bore and the engagement pocket. The engagement assembly further includes a biasing member disposed within the transverse bore and surrounding the motion inhibitor. The biasing member is configured to bias the motion inhibitor away from the engagement pocket. The engagement pocket further includes a lip that acts as stop, limiting the pivotal motion of the spinal fixation rod disposed in the engagement pocket.

BRIEF DESCRIPTION OF THE DRAWINGS

The foregoing summary, as well as the following detailed description of preferred embodiments of the application, will be better understood when read in conjunction with the appended drawings. For the purposes of illustrating the surgical instrument for introducing a spinal fixation rod of the present application, the drawings merely show exemplary embodiments. It should be understood, however, that the application is not limited to the precise arrangements and instrumentalities shown. In the drawings:

FIG. 6A is an exploded perspective view of the engagement assembly illustrated in FIG. 2, the engagement assembly including an engagement body, a lock and a biasing member;

FIG. 7A is a side elevation view of the spinal fixation rod illustrated in FIG. 2;

FIG. 7B is a perspective view of the spinal fixation rod illustrated in FIG. 7A;

FIG. 8A is a perspective view of the spinal fixation rod as illustrated in FIG. 2 engaged with the engagement body as shown in FIG. 6A, and the spinal fixation rod is in a first pivotal orientation;

FIG. 8B is a perspective view of the spinal fixation rod as illustrated in FIG. 2 engaged with the engagement body as shown in FIG. 6A, and the spinal fixation rod is in a second pivotal orientation;

FIG. 10A is a top elevation view of the surgical instrument illustrated in FIG. 1;

FIG. 13A is an enlarged cross-sectional perspective view of a distal portion of the surgical instrument as illustrated in FIG. 10A, taken along line 13A-13A, showing the primary shaft, the engagement assembly, and the spinal fixation rod while the surgical instrument is in a first configuration;

FIG. 13C is an enlarged cross-sectional perspective view of the distal portion of the surgical instrument as illustrated in FIG. 13A, but showing the surgical instrument in a third configuration.

DETAILED DESCRIPTION

Figure 1:
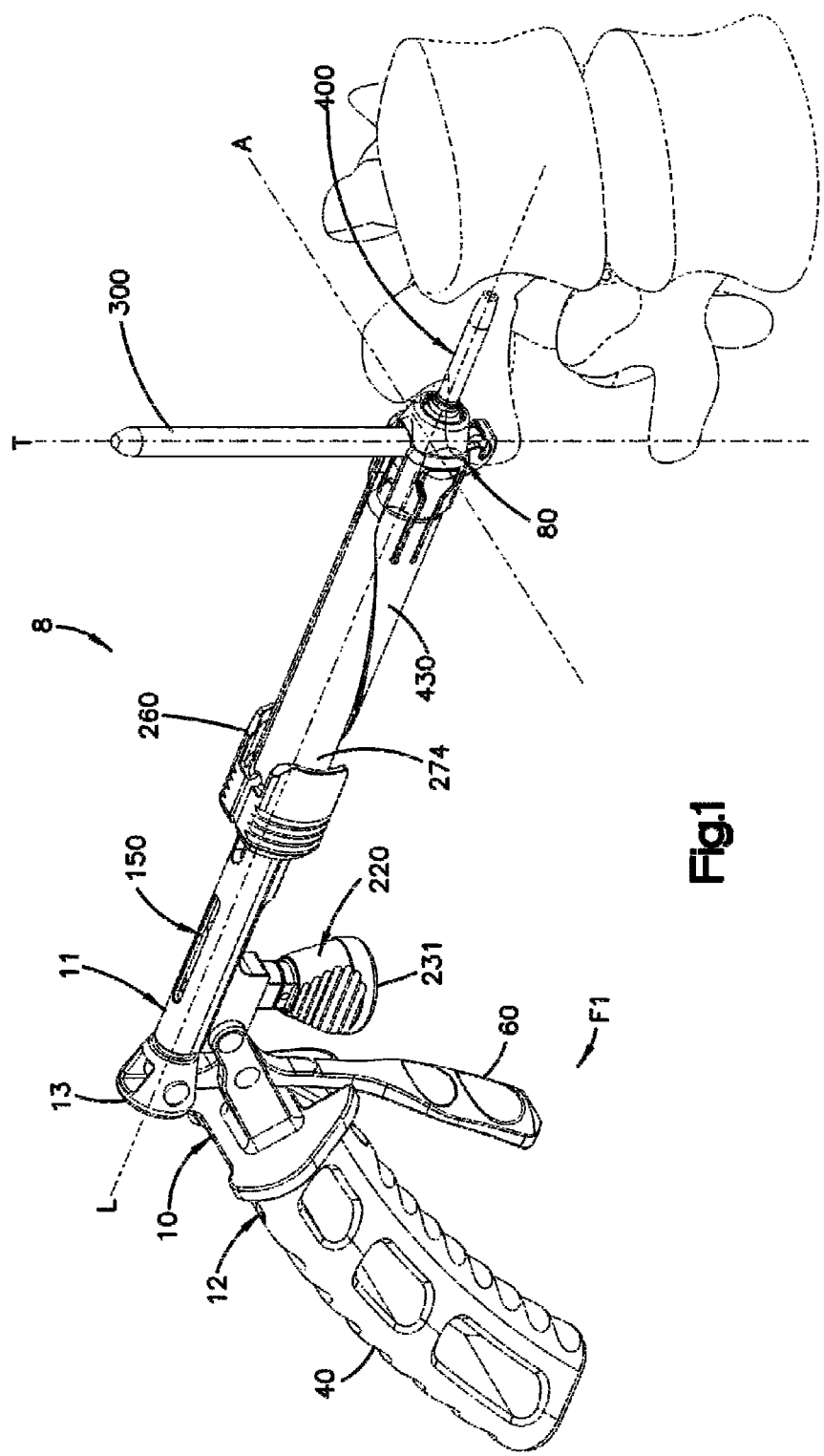
FIG. 1 is a perspective view of a surgical system constructed in accordance with one embodiment including a surgical instrument and a spinal fixation rod engaged to the surgical instrument, such that the surgical instrument is configured to insert the spinal fixation rod in a pedicle screw implanted in a vertebra.

Referring to FIG. 1, a surgical system 8 includes a surgical instrument 10, which is illustrated as a spinal fixation rod implantation tool. It is contemplated, however, that the surgical instrument 10 can be employed to implant other implants, such as different kinds of rods, tubes, or any other suitable elongate member, in other parts of a human or animal body. The surgical system 8 further includes a centering sleeve 260 that can be removably supported by the surgical instrument 10, a spinal fixation rod 300 that can be releasably engaged by the surgical instrument, a vertebral implant 400, which can be in the form of a pedicle screw that is configured to receive the spinal fixation rod 300 during operation, and a tissue retractor 430. The centering sleeve 260 is releasably secured to the surgical instrument 10 and the tissue retractor 430 so as to center the surgical instrument with respect to the tissue retractor 430 and implant the spinal fixation rod 300 at a predetermined location with respect to the vertebral implant 400. The surgical instrument 10 is illustrated as extending along a longitudinal axis L, a lateral axis A that extends substantially perpendicular to the longitudinal axis L, and a transverse axis T that extends substantially perpendicular to the longitudinal axis L and the lateral axis A. In accordance with the illustrated orientation of the surgical instrument 10, the lateral axis A and the longitudinal axis L extend horizontally, while the transverse axis T extends vertically. It can also be said that the lateral and transverse axes A and T extend radially out from the longitudinal axis L. It should be appreciated that the longitudinal, lateral, and transverse axes are used herein with reference to the orientation of the surgical instrument 10 and its components as illustrated, and that the actual orientation of the surgical instrument 10 and its components may change during use.

Figure 2:
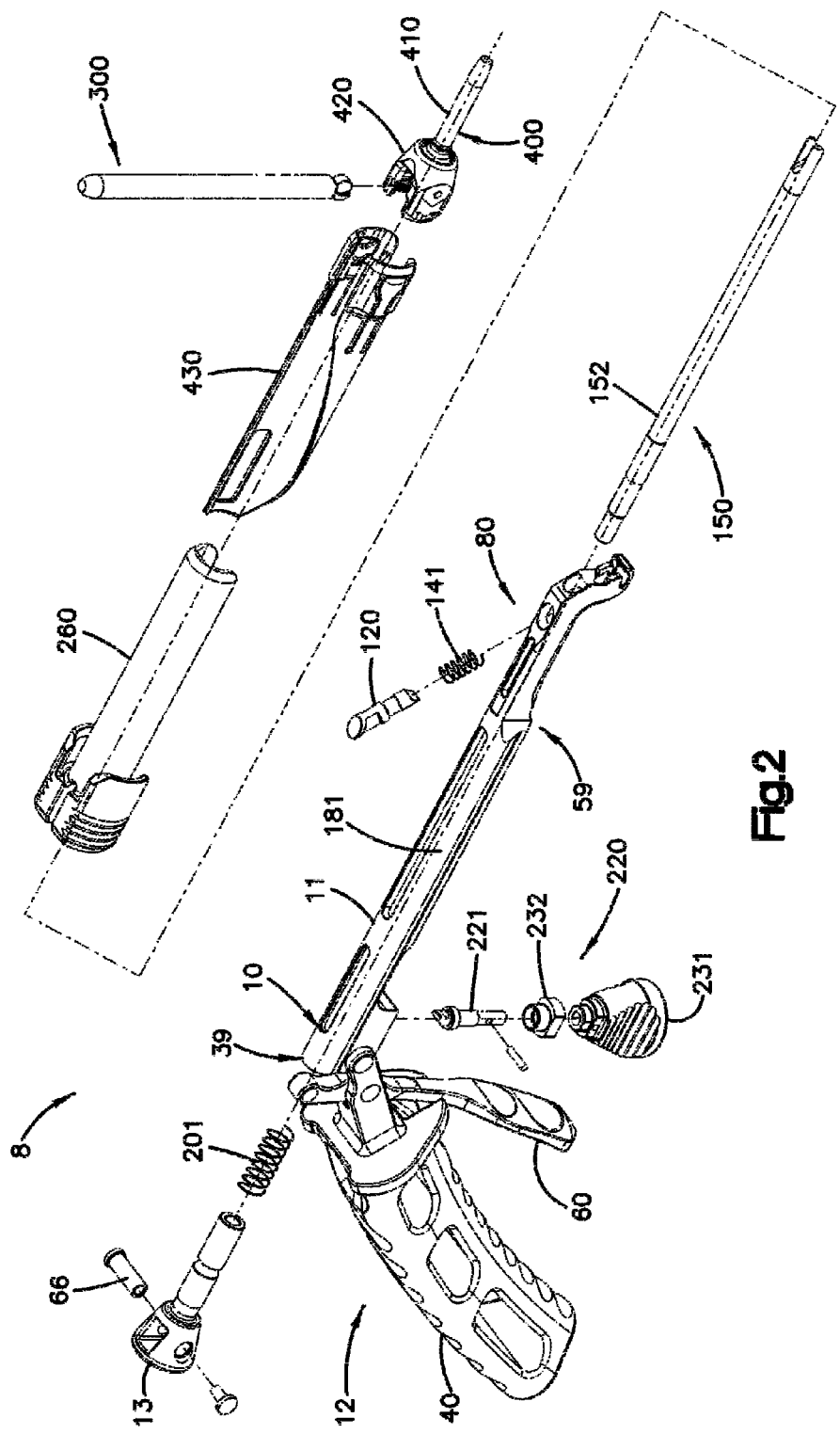
FIG. 2 is an exploded perspective view of the surgical assembly illustrated in FIG. 1, showing the surgical instrument as including a surgical instrument housing that supports an actuator assembly, an actuating mechanism, an engagement assembly, a locking mechanism, a centering sleeve, and a tissue retractor.

Referring to FIGS. 1-2, the surgical instrument 10 includes a surgical instrument housing 11 that supports an actuator assembly 12 at its proximal end 39, an engagement assembly 80 at its distal end 59, which is longitudinally opposed to the proximal end 39, and a transfer assembly 150 operatively coupled to the actuator assembly 12 and the engagement assembly 80. As used herein, forward motion refers to a direction from the proximal end 39 toward the distal end 59 of the surgical instrument housing 11, and rearward motion refers to a direction from the distal end toward the proximal end. The actuator assembly 12 can be selectively engaged and disengaged as desired in three configurations. In a first configuration, the actuator assembly 12 allows the spinal fixation rod 300 to be inserted and removed into and from the engagement assembly 80. In the second configuration, the actuator assembly 12 can be engaged so as to irremovably retain the fixation rod 300 in the engagement assembly 80. While the spinal fixation rod 300 cannot be removed from the engagement assembly 80 when the actuator assembly 12 is in the second configuration rod, the spinal fixation rod can nonetheless pivot with respect to the surgical instrument housing 11. In the third configuration, the actuator assembly 12 can be further engaged, causing the transfer assembly 150 to bias the engagement assembly 80 to a position in which the spinal fixation rod 300 is braked with respect to pivotal movement relative to the surgical instrument housing 11. Thus, when the actuator assembly 12 is in the third configuration, the engagement assembly 80 precludes, or at least inhibits, pivotal movement of the spinal fixation rod 300 relative to the surgical instrument housing 11.

Figure 3:
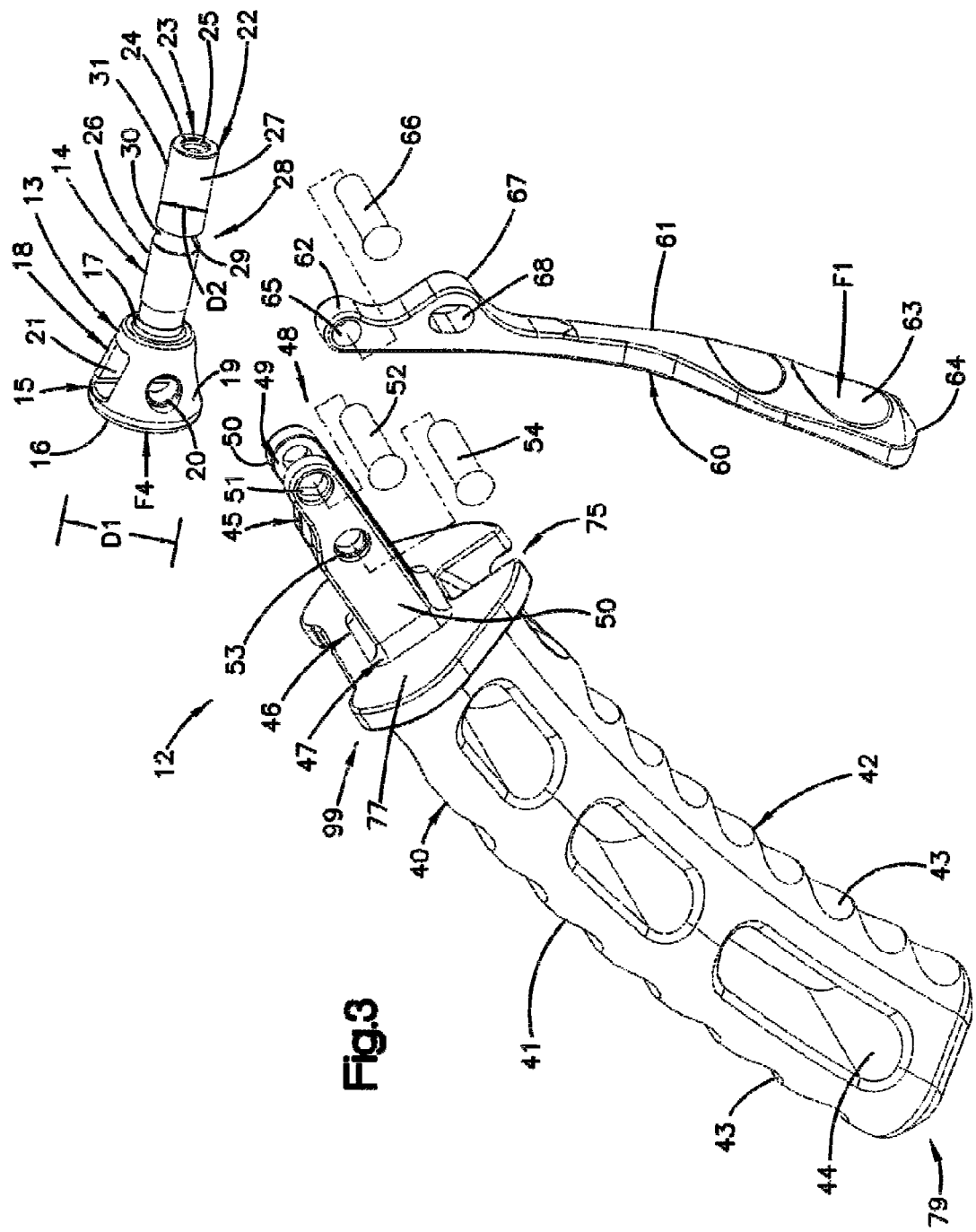
FIG. 3 is a perspective view of the actuator assembly illustrated in FIG. 2, including an actuator, a grip, and a biasing member.

Referring to FIG. 3, the actuator assembly 12 includes an actuator 13, a grip 40, and a biasing member 60. The actuator 13 is operably coupled to the primary shaft (see FIG. 2) and includes an actuator body 14 that defines a first proximal end 15 and a longitudinally opposed second distal end 22. The actuator body 14 includes a plug 18 at the proximal end 15 and a longitudinally elongate shaft 26 that extends distally from the plug 18. The plug 18 defines an outer biasing surface 16 at its proximal end, and an outer stop surface 17 at its distal end. The shaft 26 extends from the stop surface 17 and defines a diameter or cross-sectional dimension less than that of the stop surface 17. The biasing surface 16 is configured to receive a longitudinally directed force F4 and can be flat or otherwise ergonomically contoured so as to be comfortably biased by a human finger. For instance, the biasing surface 16 may have substantially concave shape. Alternatively, the biasing surface 16 may be curved or textured and sized to be biased by a biasing member or other tool. The plug 18 defines an outer surface 19 that extends between the biasing surface 16 and the stop surface 17. In accordance with the illustrated embodiment, the outer surface 19 can be round having an outer diameter D1 that tapers, decreasing as it approaches the stop 17. The configuration of the outer surface 19 may therefore provide the plug 18 with a substantially frusto-conical shape. Alternatively, it should be appreciated that the plug 18 could define any suitable alternative shape as desired.

The actuator 13 can further include a channel 21 that extends transversely into, and through, the plug 18, and is configured to receive a portion of the biasing member 60 as described in more detail below. In the illustrated embodiment, the channel 21 of the plug 18 is oriented substantially parallel to the transverse axis T defined by the surgical instrument 10 (see FIG. 1). The actuator 13 further includes an engagement member in the form of an aperture 20 that extends laterally through the plug 18 in alignment with the channel 21. The aperture 20 is configured to engage with a complementary engagement member of the biasing member so as to connect and operably couple the biasing member 60 and the plug 18. In the depicted embodiment, the aperture 20 of the plug 18 is oriented substantially parallel to the lateral axis A defined by the surgical instrument 10 (see FIG. 1). It should be appreciated that the channel 21 and the aperture 20 can extend partially through the plug 18 at different angles than described and can be any of a number of shapes such as but not limited to round, square, rectangular, or other polygonal shapes.

The shaft 26 can include a tubular or alternatively shaped body 31 that presents an outer surface 27 and defines an outer diameter D2, which can be constant or can be variable along the length of the body. The shaft 26 can also include a recess 28 that extends radially into the shaft body 31 so as to define a reduced diameter with respect to the diameter D2. The recess 28 is defined by a side surface 29 that extends radially in from the outer surface 27 and a tapered surface 30 that extends radially in from the outer surface 27 and is tapered toward the side surface 29 (see FIG. 5B). In the illustrated embodiment, the recess 28 is annular and extends radially around the entire perimeter of the body 31. However, the recess 28 may have any suitable shape or configuration. For example, the recess 28 may only extend along a bottom portion of the body 31. Regardless of its shape and configuration, the recess 28 is configured to releasably receive the release knob 231 as described in more detail below.

The actuator 13 further includes an engagement member 23 carried by the shaft 26, which can be provided as a threaded bore 24 that extends longitudinally into the second end 22 of the shaft 26. The bore 24 presents internal threads 25 configured to couple the shaft 26, and thus the actuator 13, to the transfer assembly 150 (see FIG. 4). It should be appreciated that the engagement member 23 can be provided as any structures configured to mate with a corresponding feature on the transfer assembly 150. For example, the engagement member 23 may be part of a snap-fit mechanism capable of connecting the shaft to the transfer assembly 150.

With continuing reference to FIG. 3, the actuator assembly 12 further includes a grip 40. The grip 40 includes a grip body 41, which serves as a handle for holding and manipulating the surgical instrument 10. The grip body 41 includes a gripping portion 42 and an attachment portion 45. The gripping portion 42 has a first free end 79 and a longitudinally opposed second end 99 connected to the attachment portion 45 and can be a pistol grip shape as shown or alternatively any other shape configured to be easily and comfortably grasped by a human hand. The gripping portion 42 can include one or more grooves 43 disposed on the grip body 41. As shown in the illustrated embodiment, a plurality of grooves 43 may be disposed substantially along the entire length of the grip portion 41 between the first end 79 and the second end 99. Irrespective of the number of grooves 43, each groove 43 is configured and sized to receive one or more human fingers to enhance the comfort of use and the level of control of the actuator assembly 12. In the depicted embodiment, the grooves 43 have a substantially concave configuration. The grip 40 can also include one or more cutouts 44 that extend laterally through the gripping portion 42. The cutouts 44 of the grip 40 can be configured as desired to provide a desired weight balance while also reducing the total weight of the grip 40. In addition to the cutouts 44, the grip 40 may include a guard or stop 77 at its second end 99 for preventing, or at least inhibiting, a user's hand grabbing the gripping body 41 from slipping past the second end of the grip, thereby facilitating manual control of the surgical instrument 10. As illustrated, the guard 77 features a substantially planar configuration extending laterally from the second end 99 of the grip 40 and has an open recess 75 configured and sized to receive a portion of the biasing member 60.

The attachment portion 45 extends generally up from the guard 77 and includes an attachment body 46 that defines a first lower proximal end 47 and a second upper distal end 48. The attachment portion 45 is attached to the guard 77 at the proximal end 47 and to the surgical instrument housing 11 at the distal end 48. The second end 48 defines a gap 49 that extends from the second end 48 through at least a portion of the attachment body 46 so as to define opposed attachment forks 50 separated by the gap 49. The attachment forks 50 are substantially parallel to each other and are configured to attach the grip 40 to both the surgical instrument housing 11 and the biasing member 60.

Figure 5A:
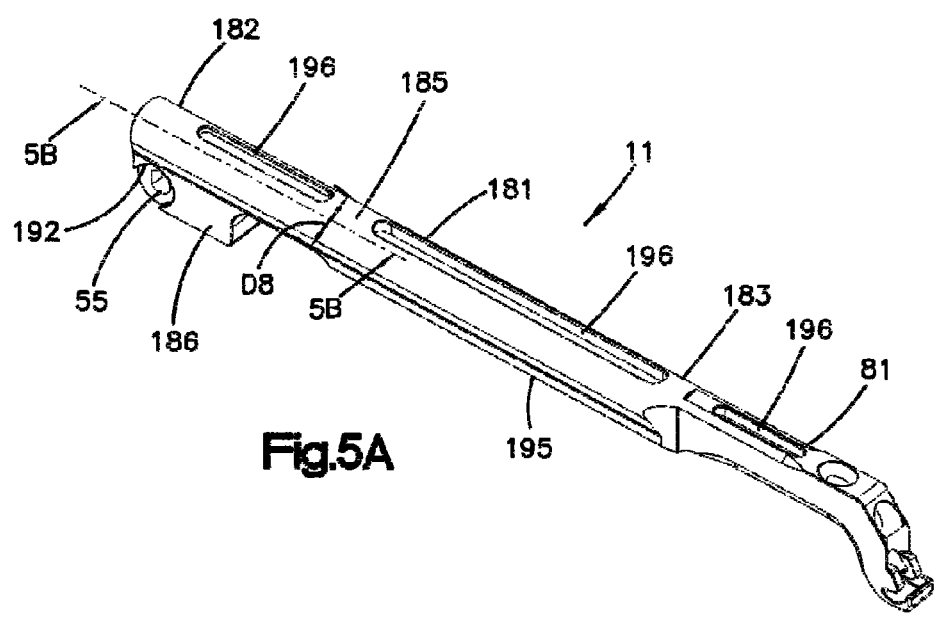
FIG. 5A is a perspective view of the surgical instrument housing illustrated in FIG. 2.

In particular, the grip 40 defines a first engagement member in the form of an outer aperture 51 that extends transversely through the attachment forks 50 and is configured to accept a first fastener 52 to connect the grip 40 to the surgical instrument housing 11, as illustrated in FIG. 1. The first fastener 52 may include any suitable device or mechanism capable of coupling the grip 40 to the surgical instrument housing 11. For example, the first fastener 52 may include a pin. As illustrated in FIG. 5A, the surgical instrument 10 defines a complementary engagement member in the form of an aperture 55 that extends transversely through the surgical instrument housing 11. Thus, the forks 50 are placed over the instrument housing 11 such that the apertures 51 and 55 are in alignment, and the fastener 52 is inserted through the apertures 51 and 55 so as to attach the grip 40 to the instrument housing 11. The instrument housing 11 can be grooved, such that the forks 50 are received in indented slots 192. The indented slots 192 are therefore configured and dimensioned to receive the forks 50. When the forks 52 are positioned in the indented slots 192 and the first fastener 52 is inserted through the apertures 51 and 55, the position of the grip 40 is fixed relative to the surgical instrument housing 11, as described in more detail below. Referring again to FIG. 3, the grip 40 can further define a second or inner aperture 53 that extends laterally through the attachment forks 50 at a location proximal of the outer aperture 51. The inner aperture 53 is configured to connect the grip 40 to the biasing member 60.

In particular, the biasing member 60 includes a biasing member body 61, which provides a lever that defines a first upper proximal end 62 and an opposed second lower distal end 64. The proximal end 62 of the biasing member body 61 is sized to fit within the channel 21 of the plug 18. The biasing member 60 includes an engagement member in the form of an aperture 65 that extends laterally through the biasing member body 61 at the proximal end 62. The proximal end 62 is inserted into the transverse channel 21 of the plug 18, such that the aperture 65 is aligned with the aperture 20. A fastener 66 is inserted through the apertures 65 and 20 so as to attach the biasing member 60 to the actuator 13. As illustrated, the fastener 66 may include a pin.

The biasing member body 61 further defines a pivot portion 67 disposed between the proximal end distal ends 62 and 64. The pivot portion 67 is sized to fit in the gap 49 of the grip 40. The biasing member body 61 defines an engagement member in the form of an aperture 68 that extends laterally through the pivot portion 67. The pivot portion 67 is inserted into the gap 49 of the grip 40 between the attachment forks 50, such that the aperture 68 is aligned with the inner aperture 53 of the grip 40. A fastener 54, such as a pin, is inserted through the apertures 68 and 53 so as to pivotally attach the biasing member 60 to the grip 40.

During use, a surgeon can grab onto the grip 40 in order to manipulate the actuator assembly 12, and simultaneously grasp the distal end 64 of the biasing member body 61. The distal end 64 can present one or more gripping grooves 63 as desired. Each gripping groove 63 is configured and sized to receive one or more user's fingers. To this end, each gripping groove 63 may have a concave configuration. A force F1, which can be a manual squeeze, can be applied to the distal end 64 of the biasing member 60 to bias the distal end 64 toward the grip 40, causing the biasing member body 61 to pivot about the fastener 54. This pivotal movement of the biasing member body 61 in turn causes the proximal end 62 to move longitudinally forward. Because the proximal end 62 of the biasing member 60 is coupled to the actuator 13, the force F1 causes the biasing member 60 to bias the actuator 13 in a forward direction, which also causes the transfer assembly 150 (see FIGS. 1 and 4) to translate longitudinally forward. Alternatively, a longitudinally forward force F4 can be applied directly to the biasing surface 16 of the plug 18 so as to urge the actuator 13 and transfer assembly 150 forward. In this regard, it should be appreciated that the surgical instrument 10 can be provided without the biasing member 60.

Figure 4:
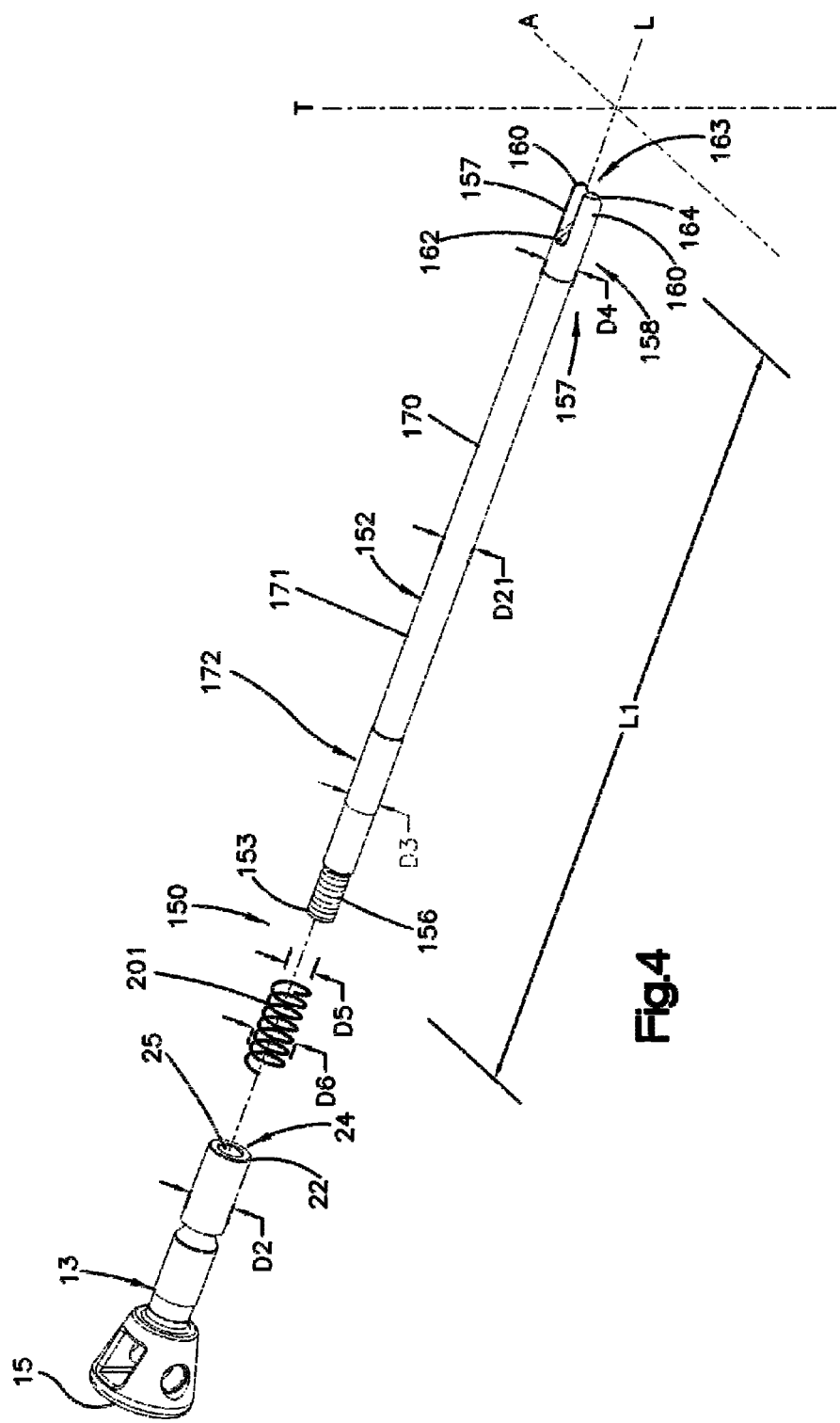
FIG. 4 is a perspective view of the transfer assembly and the actuator illustrated in FIG. 2, the transfer assembly including a shaft and a biasing member.

Referring now to FIG. 4, the transfer assembly 150 includes an actuation member in the form of a primary shaft 152 that includes a longitudinally elongate shaft body 170 defining a first proximal end 153 and an opposed second distal end 157. The primary shaft 152 defines an engagement member provided as external threads 156 on the proximal end 153 of the shaft body 170. The threads 156 correspond to, and are configured to mate with, the internal threads 25 within the inner bore 24 of the actuator 13 so as to releasably connect the primary shaft 152 to the actuator 13. Accordingly, to secure the primary shaft 152 to the actuator 13, the shaft body 170 is aligned with the inner bore 24 and then the primary shaft 152 and the actuator 13 are rotated with respect to one another, thereby causing the threads 156 and 25 to mate. The effective length of the coupled primary shaft 152 and actuator 13 can be adjusted by how far the post primary shaft 152 is screwed into the inner bore 24. The threaded connection allows the effective length to be adjusted as desired to correct for variances in tolerances of the manufactured parts of the surgical instrument 10. As discussed above, the threads 156 and 25 may be replaced by any other device, apparatus or mechanism suitable for releasably connecting the shaft 152 to the actuator 13.

The elongate body 170 has a rod-like shape that defines a longitudinal length L1 and presents an outer surface 171 that extends radially outward from the longitudinal axis L. The outer surface 171 can be round or otherwise shaped as desired, extends along a portion of the longitudinal length L1 of the elongate body 170, and defines an outer diameter or cross-sectional dimension D21. The elongate body 170 defines a raised portion 172 that presents an outer diameter D3 or cross-sectional dimension that is larger than the outer diameter or cross-sectional dimension D21 defined by the outer surface 171. Alternatively, the outer diameter D21 defined by the outer surface 171 may be equal or substantially similar to the outer diameter or cross-sectional dimension D3 of the raised portion 172. In other embodiments, the outer diameter or cross-sectional dimension of the elongate body 170 remains constant along the length L1.

The primary shaft 152 includes an engagement member provided as a connection link 158 at the second end 157 of the shaft body 170. The connection link 158 has a round shape or any other suitable shape and has an outer diameter or cross-sectional dimension D4. In the depicted embodiment, the outer diameter or cross-sectional dimension D4 of the connection link 158 is greater than the outer diameter or cross-sectional dimension D21 defined by outer surface 171 and substantially similar to the outer diameter or cross-sectional dimension D3 of the raised portion 172. In alternative embodiments, the outer diameter or cross-sectional dimension D4 of the connection link 158 is substantially similar to the outer diameter or cross-sectional dimension D21 defined by the outer surface 171. The primary shaft 152 defines a gap 163 extending longitudinally into the second end 157 of the shaft body 170 so as to define opposed tips 160. The gap 163 terminates at a beveled shaft surface 162 that is sloped transversely downward along a longitudinally forward direction. The opposing tips 160 each include a curved engagement surface 164 that is configured to operatively couple the primary shaft 152 to the engagement assembly 80 (see FIG. 2), as described in more detail below.

With continuing reference to FIG. 4, the transfer assembly 150 further includes a biasing member, which can be a coil spring 201 that defines an inner diameter or cross-sectional dimension D5 and an outer diameter or cross-sectional dimension D6. The inner diameter D5 is greater than the outer diameter D3 of the raised portion 172 of the elongate shaft body 170 and less than the outer diameter D2 of the actuator 13. This allows the primary shaft 152 to be disposed within the spring 201 and prevents, or at least inhibits, the actuator 13 from being disposed within the spring 201. The spring 201 can be captured between the distal end 22 of the actuator 13 and a seat 197 of the surgical instrument housing 11 (see FIG. 5B). Accordingly, the spring 201 provides a spring force that biases the actuator 13 longitudinally rearward toward its disengaged position, such that forward motion of the actuator 13, and thus the primary shaft 152, relative to surgical instrument housing 11 is against the spring force.

Figure 5B:
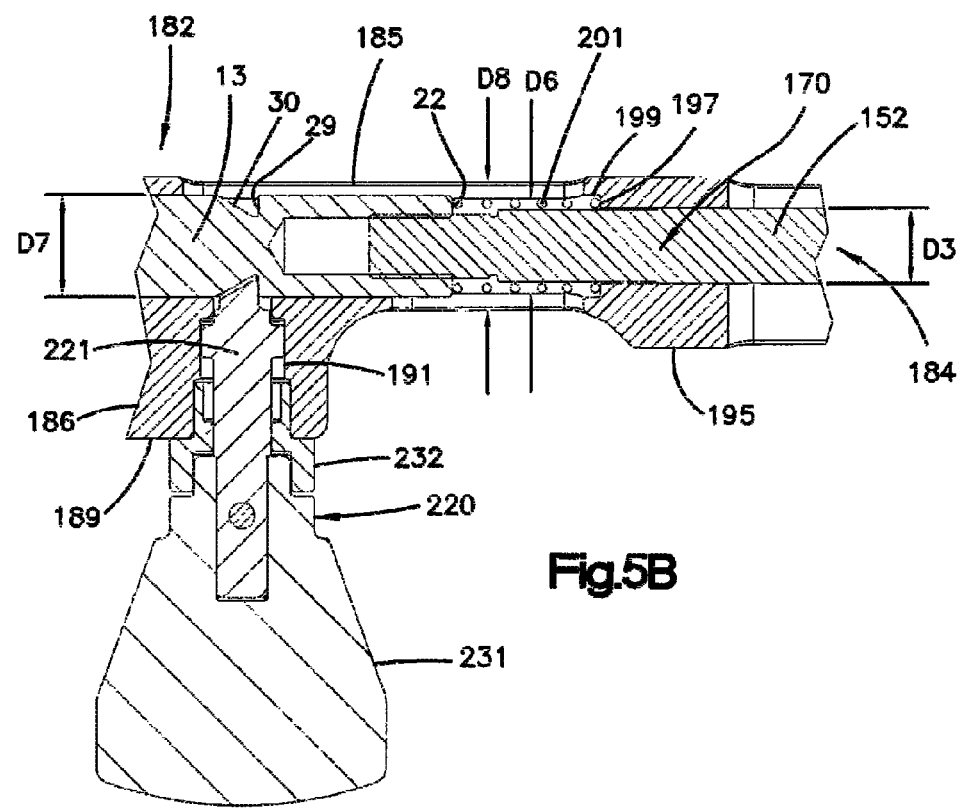
FIG. 5B is a cross-sectional view of the housing as illustrated in FIG. 5A, taken along line 5B-5B, showing an actuator, engagement member and biasing member supported by the housing.

Referring to FIGS. 5A and 5B, the surgical instrument housing 11 includes a longitudinally elongate tubular body 181 that defines a first proximal end 182 and a longitudinally opposed second distal end 183. The proximal end 182 is attached to the grip 40 as described above with reference to FIGS. 2 and 3. The surgical instrument housing 11 further includes an engagement body 81 that is attached, for instance monolithically attached, to the second end 183 of the tubular body 181. The tubular body 181 defines an inner bore 184 which extends longitudinally between and through the proximal and distal ends 182 and 183. The proximal end 182 of the tubular body 181 defines an inner diameter or cross-sectional dimension D7 of the inner bore 184.

The housing body 181 presents an outer surface 185 that defines an outer diameter or cross-sectional dimension D8. The inner diameter D7 of the inner bore 184 is at least slightly greater than the outer diameter D6 of the spring 201, such that the spring 201 can be disposed in the inner bore 184 at the proximal end 182 of the housing body 181. The housing body 181 includes an inner shoulder 199 defining a seat surface 197 located distally of the portion of the inner bore 184 defining inner diameter D7. The seat surface 197 defines an inner diameter less than the inner diameter D7, and further less than the inner diameter D5 of the coil spring 201. Accordingly, one end of the coil spring 201 sits against the seat surface 197, and an opposed end of the coil spring 201 sits against the distal end 22 of the actuator 13 as described above. The inner diameter of the seat surface 197 is also slightly greater than the outer diameter D3 of the elongate shaft body 170, such that the shaft 152 is slidably received in the housing body 181.

The surgical instrument housing 11 includes a grip mount 186 that extends transversely down from the first end 182 of the housing body 181. Opposed lateral sides of the grip mount 186 define an indented slot 192 configured to receive the attachment forks 50 of the grip 40. The surgical instrument housing 11 further defines an aperture 55 that extends laterally through the grip mount 186 at a location aligned with the indented slots 192. To attach the grip 40 to the housing body 181 the attachment forks 50 are slid into the indent slots 192 until the outer aperture 51 of the grip 40 is aligned with the aperture 55 of the surgical instrument housing 11 (see also FIG. 3). The fastener 52 is then inserted through the apertures 55 and 51. Once the fastener 52 has been inserted, the grip 40 and the housing body 181 are attached and unable to rotate with respect to one another. The surgical instrument housing 11 further defines a transverse aperture 191 that extends into the bottom end of the grip mount 186 and into the inner bore 184 of the housing body 181. The grip mount 186 is configured to support a locking mechanism 220, such that a locking shaft 221 of the locking mechanism extends through the second aperture 191, as described in detail below (see FIG. 9).

The surgical instrument housing 11 can also include a longitudinally elongate projection 195 that extends transversely down from the housing body 181. The projection 195 provides additional strength and rigidity to the housing body 181. Additionally, the surgical instrument housing 11 can define a number of openings 196 located as desired which extend from the outer surface 185 into the inner bore 184. The openings 196 can have an elongate slot shape as shown and can facilitate cleaning and sterilization of the surgical instrument 10. Thus, one of skill in the art will realize that the size, shape and orientation of the openings 196 can vary as desired. In another alternative embodiment, the surgical instrument housing 11 can have no openings 196. As discussed in detail below with respect to FIG. 12, the surgical system 8 may include a centering sleeve 260 (see FIGS. 1 and 12) that can be releasably secured to the surgical instrument 10 and the tissue retractor 430 so as to center the surgical instrument with respect to the tissue retractor 430 and implant the spinal fixation rod 300 at a predetermined location with respect to the vertebral implant 400. The surgical system 8 can be used without the centering sleeve 260 and, in such a case, the projection 195 of the surgical instrument housing 11 can act as a centering spacer when the surgical instrument housing is placed within the tissue retractor 430 so as to center the surgical instrument 10 relative to the tissue retractor 430 and implant the spinal fixation rod 300 at a predetermined position with respect to the tissue retractor 430.

Figure 6B:
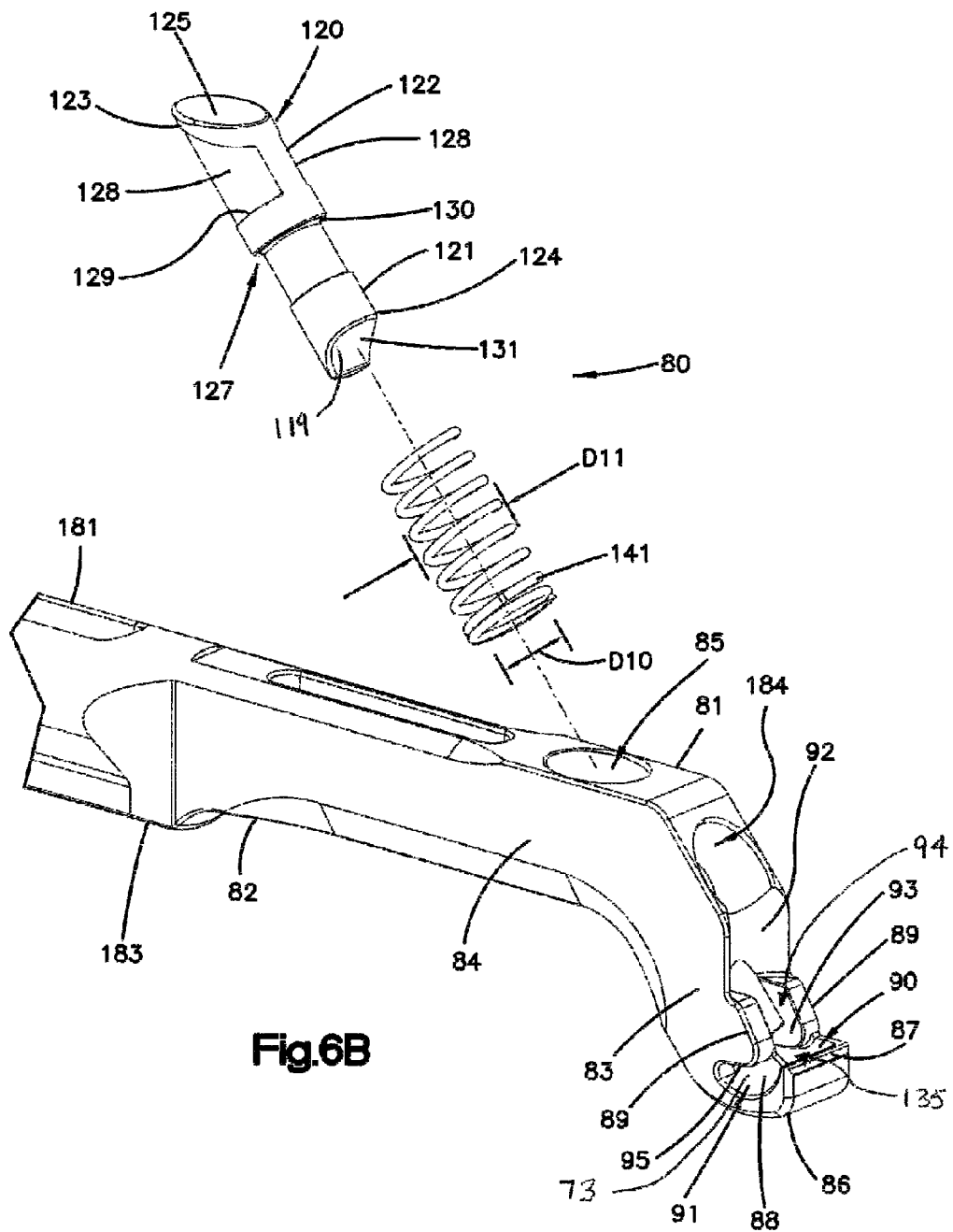
FIG. 6B is another exploded perspective view of the engagement assembly illustrated in FIG. 6A.

Referring to FIGS. 6A and 6B, the engagement assembly 80 includes the engagement body 81 of the surgical instrument housing 11, a spinal fixation rod motion inhibitor or brake 120, and a biasing member which can be provided as a coil spring 141. The motion inhibitor 120 is operably coupled to the primary shaft 152 (see FIG. 2). The engagement body 81 defines a first proximal portion 82 attached to the second end 183 of the housing body 181 and a second distal portion 83 that extends longitudinally forward and transversely down from the first proximal portion 82. The transverse offset of the second distal portion 83 relative to the first proximal portion 82 facilitates proper positioning of the spinal fixation rod 300 (see FIG. 8A) when implanted in a plurality of pedicle screws within the patient's body. The engagement body 81 presents an outer surface 84 and also defines a transverse bore 85 that extends transversely down into the outer surface 84 of the proximal portion 82, intersects the inner bore 184 of the housing body 181, and terminates in the second distal portion 83.

The second distal portion 83 includes an engagement tip 86, which defines an outer lip 87, a first engagement wall 73 that carries a corresponding first engagement surface 88, which can be a curved or concave lower surface, extending into the interior of the second distal portion 83 from the lip 87 and laterally opposed retaining walls 89. The lip 87, lower surface 88 and opposing retaining walls 89 form an engagement pocket 90. The curvature of the lower surface 88 substantially matches the curvature of an end portion of the spinal fixation rod 300 so that such end portion of the spinal fixation rod can be securely retained within the pocket 90. The pocket 90 extends into the engagement body 81 and intersects with the inner bore 85. The retaining walls 89 define laterally opposed vertical interior surfaces 93. The interior surfaces 93 are connected by a curved or concave lateral beam 92 disposed in the second distal portion 83. The curved lateral beam 92 can be contoured so as to match the outer curved surface of the spinal fixation rod 300.

The retaining walls 89 each further includes a bottom surface 95 that is curved in a substantially vertical plane. The lower surface 88 and the bottom surface 95 are separated and define a retention gap 91 therebetween. The retention gap 91 is shaped to receive a corresponding surface of the spinal fixation rod 300 such that once the spinal fixation rod 300 is engaged within the pocket 90, the spinal fixation rod 300 can only be removed from the pocket 90 when the spinal fixation rod 300 is oriented substantially perpendicular to the longitudinal and lateral axes L and A and substantially parallel to the transverse axis T defined by the surgical instrument 10 (see FIG. 1). In alternate embodiments, once the spinal fixation rod 300 has been positioned within the pocket 90, it can only be removed from the pocket when oriented in other positions or orientations. For instance, in some embodiments, the spinal fixation rod 300 can only be removed from the pocket 90 when the spinal fixation rod is oriented substantially parallel to the longitudinal axis L defined by the surgical instrument 10 (see FIG. 1). In yet other embodiment, the spinal fixation rod 300 can only be withdrawn from the pocket 90 when it is oriented at an angle relative to the transverse axis T defined by the surgical instrument 10 (see FIG. 1). Although the spinal fixation rod 300 cannot be removed from the pocket 90 when oriented at a particular orientation, as discussed above, the curvature of the lower surface 88 and the configuration of the bottom surface 95 of the engagement assembly 80 allow the spinal fixation rod 300 to pivot relative to the engagement tip 86 between a first position and a second position. In the first position, the spinal fixation rod 300 is oriented substantially parallel to the transverse axis T, whereas, in the second position, the spinal fixation rod is oriented at an obtuse angle relative to the longitudinal axis L. The first and second positions of the spinal fixation rod 300 may nevertheless vary in other embodiments. For example, in alternate embodiments, the spinal fixation rod 300 may be oriented substantially parallel to the longitudinal axis L when located in the second position.

The motion inhibitor or brake 120 defines an auxiliary shaft 121 that is a rod-like member having an outer diameter or cross-sectional dimension D9. The auxiliary shaft 121 is disposed within the inner bore 85; thus, the outer diameter D9 is smaller than the diameter or cross-sectional dimension of the inner bore 85. The auxiliary shaft 121 also includes an auxiliary shaft body 122 that defines a first proximal end 123 and an opposed second distal end 124. The proximal end 123 defines a top surface 125, which is shaped such that, when the auxiliary shaft 121 is at rest with no external forces acting upon it and disposed within the inner bore 85, the top surface 125 is substantially parallel to, and recessed within, the outer surface 84 of the first portion 82 of the engagement body 81. The motion inhibitor 120 defines cutouts extending into the auxiliary shaft body 122 so as to define an indented portion 128 that has a reduced cross-sectional dimension D20 relative to the rest of the auxiliary shaft 121. The indented portion 128 defines a pair of engagement surfaces 129 configured to engage the curved engagement surface 164 on the tips 160 of the primary shaft 152 (see FIG. 4). The distal end 124 of the auxiliary shaft body 122 has a reduced outer diameter or cross-sectional dimension D9 compared to the first end 123. This abrupt change in outer diameter D9 occurs at a transition 127, which provides a spring seat 130. The distal end 124 terminates at a second engagement wall 119 that defines a corresponding second engagement surface 131, which can be defined as a curved or concave brake surface as illustrated, which may be substantially concave.

The engagement assembly 80 defines a variable-sized rod receiving gap 94 that can be shaped and sized to receive a portion of the spinal fixation rod 300 and to permit the spinal fixation rod to pivot inside the pocket 90 when the rod receiving gap 94 defines a first size, and further to retain a portion of the spinal fixation rod 300 when the rod receiving gap 94 defines a second size that is less than the first size (see FIGS. 8A-B). The rod receiving gap 94 is further configured to define a third size that is less than the second size, such that the engagement assembly 80 can prevent movement of the spinal fixation rod 300 inside the rod receiving gap 94. The rod receiving gap 94 can be defined by and between the first engagement wall 73, and thus the corresponding first engagement surface 88, and the second engagement wall 119, and thus the corresponding second engagement surface 131. As is described in more detail below, at least one of the first and second engagement walls 73 and 119 is movable toward the other from a first position to a second position so as to change the size of the rod receiving gap 94 from the first size to the second size, respectively, and further from the second position to a third position so as to change the size of the rod receiving gap 94 from the second size to the third size. For instance, the primary shaft 152 is operably coupled to the movable engagement wall 119, such that translation of the primary shaft 152 causes the movable engagement wall 119 to move with respect to the other engagement wall 73. The engagement assembly 80 further defines an ejection port 135 shaped and sized to receive a portion of the spinal fixation rod 300. The ejection port 135 is in communication with the rod receiving gap 94 and can be defined by and between the retaining walls 89 and the lip 87. In the depicted embodiment, the ejection port 135 faces a direction substantially perpendicular to a longitudinal axis L (see FIG. 1) defined along the length of the surgical instrument 10 to removal of the spinal fixation rod 300 from the engagement pocket 90 only when the spinal fixation rod is substantially perpendicular to the longitudinal axis L defined by the surgical instrument 10 and when at least one of the first and second engagement walls 73 and 119 is in the first position. At least one of the retaining walls 89 and a lip 87 extend substantially perpendicular to the longitudinal axis L defined along the length of the surgical instrument at the ejection port 135.

The curvature of the curved brake surface 131 is substantially equal to the curvature of a curved top brake surface 311 of a brake 307 of the spinal fixation rod 300 (see FIGS. 7A-B). The top brake surface 311 of the brake 307 may have a substantially convex shape. As discussed in detail below, the motion inhibitor 120 can move along a first or disengaged position, a second or engaged position, and a third or braking position. When the motion inhibitor 120 is in the first position, the rod receiving gap 94 (see FIGS. 6A-B) has a first size and the curved brake surface 131 is positioned outside the engagement pocket 90. Consequently, the curved brake surface 131 does not engage or contact the curved top surface 311 of the spinal fixation rod 300. In the second position, the motion inhibitor 120 is at least partially positioned inside the engagement pocket 90 and the rod receiving gap 94 (see FIGS. 6A-B) has a second size, which is less than its first size when the motion inhibitor 120 is in the first position. Additionally, when the motion inhibitor 120 is in the second position, its brake surface 131 abuts or contacts the curved top surface 311 of the spinal fixation rod 300, thereby preventing removal of the spinal fixation rod 300 from the pocket 90. When the motion inhibitor 120 is in the third position, the rod receiving gap 94 (see FIGS. 6A-B) has a third size, which is less than its second size when the motion inhibitor 120 is in the second position. Moreover, when the motion inhibitor 120 is in the third position, its brake surface 131 functions as a brake and the curved brake surface 131 exerts pressure against the curved top surface 311 of the spinal fixation rod 300 to prevent, or at least inhibit, the spinal fixation rod 300 from pivoting with respect to the surgical instrument 10.

The spring 141 defines an inner diameter or cross-sectional dimension D10 and an outer diameter or cross-sectional dimension D11. The inner diameter D10 of the spring 141 is greater than the reduced outer diameter D9 of the second end 124 of the auxiliary shaft 121 and less than the cross-sectional dimension D20 of the first end 123 of the auxiliary shaft 121. The inner diameter D10 of the spring 141 is also greater than a portion of the inner bore 85 located in the second distal portion 83 of the engagement body 81 and adjacent a seat 169 (see FIG. 11A). The outer diameter D11 of the spring 141 is greater than its inner diameter D10 but smaller than the diameter of the inner bore 85. The spring 141 can therefore be disposed within the inner bore 85, such that the distal end 124 of the auxiliary shaft 121 is disposed within the spring 141 and the proximal end of the spring 141 seats against the spring seat 130. The engagement body 81 further defines a seat 169 in its second distal portion 83 for the spring 141 disposed within the inner bore 85, such that the spring 141 extends between the seat 169 in the bore 85 and the spring seat 130 (see FIG. 11A). The spring 141 provides a spring force that biases the motion inhibitor or brake 120 proximally, away from the pocket 90 of the engagement assembly 80. Hence, if a spinal fixation rod 300 is partially disposed within the pocket 90, the spring 141 biases the motion inhibitor or brake 120 away from the spinal fixation rod 300. In other words, the spring 141 biases the motion inhibitor or brake 120 toward its first or disengaged position.

Referring now to FIGS. 7A-B the spinal fixation rod 300 includes a rod body 301, which presents an outer surface 302 having an outer diameter or cross-sectional dimension D12. The rod body 301 is elongate from a first proximal end 304 to a second distal end 303 along a central rod axis 317. The rod body 301 includes a nose 305 at the distal end 303, which as shown is bullet-shaped to facilitate entry into a patient's body. The spinal fixation rod 300 includes a linkage 316 that extends from the proximal end 304 of the rod body 301. The linkage 316 includes a brake 307 and at least one engagement rail 306. In the illustrated embodiment, the linkage 316 includes a pair of engagement rails 306 supported on opposite lateral sides of the brake 307. The engagement rails 306 facilitate insertion of the spinal fixation rod 300 into the pocket 90 and also inhibit inadvertent removal of the spinal fixation rod 300 from the pocket 90. The brake 307 is configured to selectively engage the motion inhibitor 120 to prevent the spinal fixation rod 300 from pivoting in the pocket 90.

The engagement rails 306 are defined by a first sloped engagement surface 308, a second sloped engagement surface 309 angularly offset with respect to the first sloped engagement surface 308, and a curved engagement surface 310 opposite the first and second sloped engagement surfaces 308 and 309. The first and second sloped engagement surfaces 308 and 309 meet at an intersection 315, and define a V-shape, which corresponds to the top surface 95 of the engagement tip 86 of the engagement assembly 80 (see FIG. 6B). The curved engagement surface 310 is shaped to correspond to the lower surface 88 of the engagement tip 86. Thus, the spinal fixation rod 300 is inserted into the pocket 90 by placing the rod 300 in a transverse orientation and inserting the engagement rails 306 into the mouth of the gap 91 between the retaining walls 89 and the lower surface 88 (FIG. 8A), and subsequently pivoting the spinal fixation rod 300 so that the engagement rails 306 are received in the gap 91 (FIG. 8B).

With continuing reference to FIGS. 6A-7B, the brake 307 includes a curved top brake surface 311 and opposing side walls 312 extending from the curved top brake surface 311, such that the engagement rails 306 project laterally out from the side walls 312. The opposing side walls 312 are separated by a distance which defines a length L2. The length L2 is sized to allow the brake 307 to fit within the gap 91 in the engagement tip 86 between the opposed retaining walls 89. The curvature of the curved top brake surface 311 of the brake 307 is substantially similar to the curvature of the curved brake surface 131 of the motion inhibitor 120. As will be appreciated from the description below, the brake surface 131 of the motion inhibitor 120 is configured to selectively act against the curved top brake surface 311, thereby preventing, or at least inhibiting, the spinal fixation rod 300 from pivoting with respect to the surgical instrument 10. Thus, the curved top brake surface 311 of the spinal fixation rod 300 can also be referred to as a brake surface.

The spinal fixation rod 300 further includes a first notch 313 and an opposed second notch 314 each extending from the outer surface 302 toward the central axis 317 at the interface between the rod body 301 and the linkage 316. The second notch 314 is sized to receive to the lip 87 of the engagement tip 86 when the maximum pivotal orientation of the spinal fixation rod 300 has been reached. In this regard, the lip 87 can be referred to as a stop that limits the pivotal movement of the spinal fixation rod 300 relative to the surgical instrument 10.

Referring now also to FIG. 8A, just as the spinal fixation rod 300 can be inserted into the pocket 90 in a first angular transverse orientation, the spinal fixation rod 300 can also be removed from the pocket 90 in the transverse orientation. When the spinal fixation rod 300 is in the first orientation as shown, a substantially transversely outwardly directed force F2 applied to the spinal fixation rod 300, or an opposite force applied to the engagement tip 86 results in the release of the spinal fixation rod 300 from the pocket 90. A force applied in any other direction will not allow the spinal fixation rod 300 to be released from the pocket 90. Laterally outward movement of the spinal fixation rod 300 within the pocket 90 is prevented by interference between the corresponding interior lateral surfaces 93 of the engagement tip 86 and the side walls 312 of the spinal fixation rod 300. Longitudinally outward movement of the spinal fixation rod 300 within the pocket 90 is prevented by interference between the corresponding outer surface 302 of the spinal fixation rod 300 and the curved lateral beam 92 of the engagement tip 86 in one direction and the corresponding curved engagement surface 310 and the lower surface 88 in the other direction. Thus, in the illustrated embodiment, the spinal fixation rod 300 is removable from the pocket 90 in only one transverse direction (i.e., when the spinal fixation rod 300 is oriented substantially parallel to the transverse axis T relative to the surgical instrument 10). As will be appreciated from the description below, the spinal fixation rod 300 can be removed only when the actuator assembly 12 is disengaged.

Referring now also to FIG. 8B, the spinal fixation rod 300 is shown engaged with the pocket 90 of the engagement tip 86 in a second orientation that is angularly offset with respect to the first orientation. In this second orientation, the spinal fixation rod 300 is oriented at an acute angle relative to the transverse axis T. When the spinal fixation rod 300 is in the second orientation, the spinal fixation rod 300 cannot be removed from the pocket 90. Lateral movement of the spinal fixation rod 300 within the pocket 90 is prevented by interference between the corresponding interior lateral surfaces 93 of the engagement tip 86 and the side walls 312 of the spinal fixation rod 300. Longitudinal movement of the spinal fixation rod 300 within the pocket 90 is prevented by interference between the corresponding second sloped engagement surface 309 of the spinal fixation rod 300 and the bottom surface 95 of the engagement tip 86 in one direction and the corresponding curved engagement surface 310 and the lower surface 88 in the other direction. Transverse movement of the spinal fixation rod 300 within the pocket 90 is prevented by interference between the corresponding curved top surface 311 (See FIG. 7B) and the brake surface 131 (or alternatively the second sloped engagement surface 309 and the bottom surface 95) in one direction and the corresponding curved engagement surface 310 and the lower surface 88 in the other direction. Thus, when the spinal fixation rod 300 is disposed within the pocket 90 in the second orientation (or any orientation other than parallel to the first direction) the spinal fixation rod 300 is not removable from the pocket 90.

Figure 9:
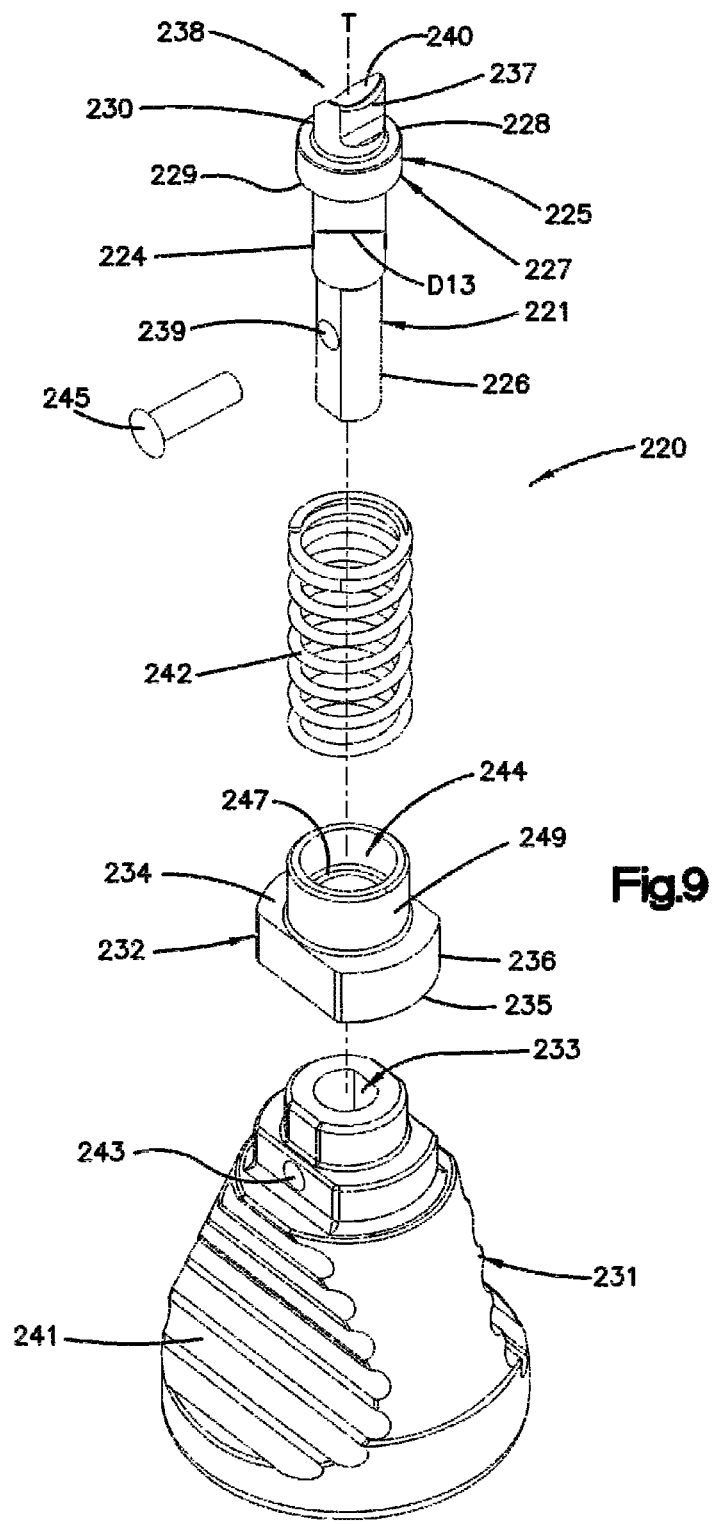
FIG. 9 is a perspective view of the locking mechanism as illustrated in FIG. 2.
Figure 10B:
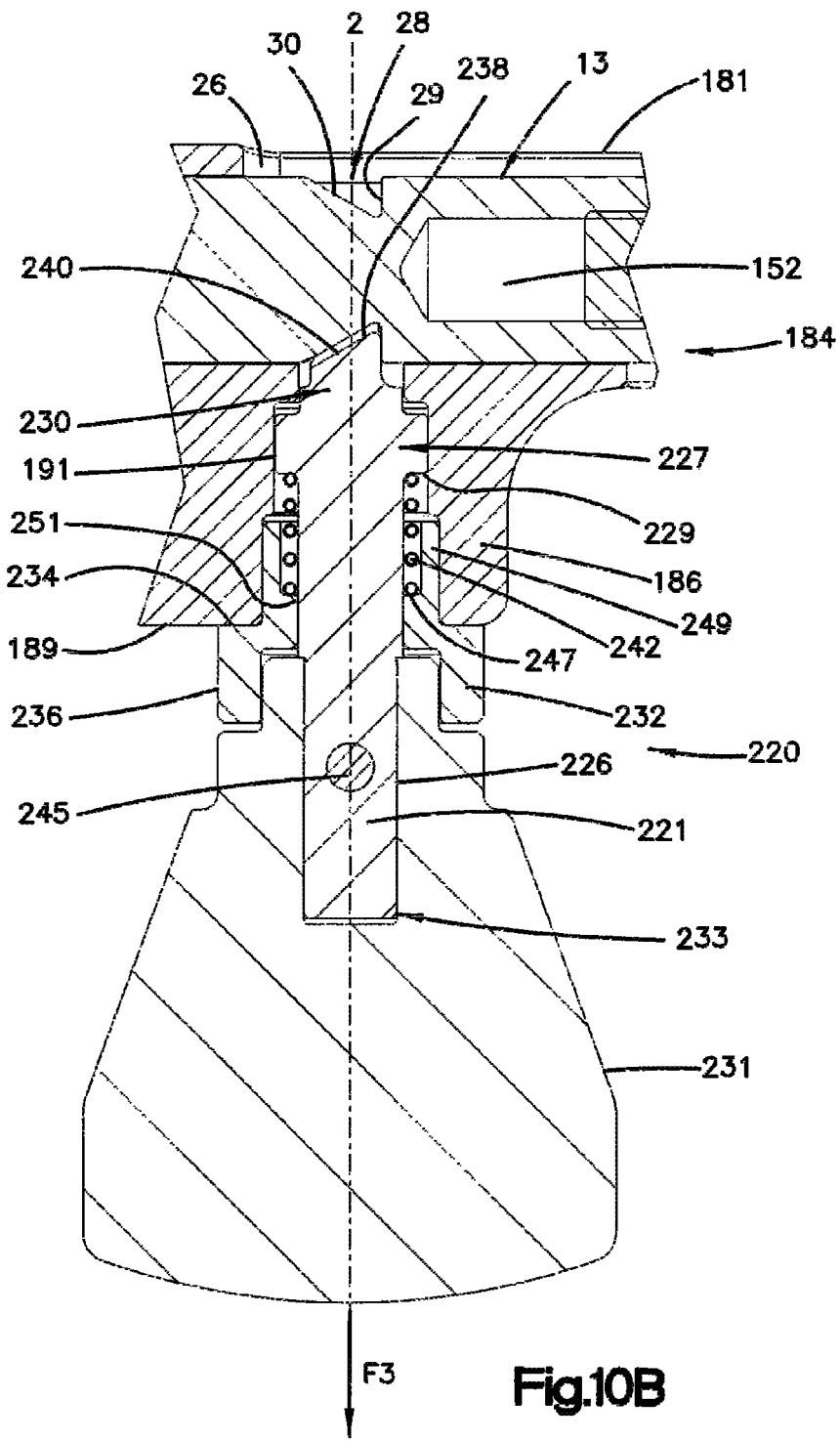
FIG. 10B is a sectional side elevation view of the surgical instrument illustrated in FIG. 10A, taken along line 10B-10B.

Referring now to FIG. 9-10B, the surgical instrument housing 11 supports a locking mechanism 220 including a locking shaft 221, a release actuator illustrated as a release knob 231 attached to the locking shaft 221, a bracket 232, and a biasing member illustrated as a spring 242 that receives the locking shaft 221. The locking shaft 221 has an outer surface 224 defining an outer diameter or cross-sectional dimension D13. The outer diameter D13 of the locking shaft 221 is sized so that the locking shaft 221 can be disposed within the transverse aperture 191 that extends into the bottom end of the grip mount 186 (see FIG. 10B). The locking shaft 221 includes a head 225 and an elongate post 226 extending from the head 225 substantially parallel to the transverse axis T. The head 225 has a collar 227 that defines a top surface 228 and a transversely opposed bottom surface 229. A key 230 extends up from the top surface 228 of the collar 227 and terminates at a channel 238. The key 230 further contains a flat transverse wall 237 and an engagement member illustrated as a curved engagement wall 240 that defines the channel 238. The engagement wall 240 is sized to fit in the recess 28 of the actuator 13. The post 226 extends down from the bottom surface 229 of the collar 227. The locking shaft 221 defines a first aperture 239 that extends laterally through the post 226. The spring 242 receives the post 226 and the outer surface 224 of the locking shaft 221, and seats against the bottom surface 229 of the collar 227.

With continuing reference to FIGS. 9-10B, the bracket 232 defines a top surface 234, a bottom surface 235, and outer perimeter 236 extending between the top and bottom surfaces. The bracket 232 is mounted (e.g., welded or otherwise attached) to the grip mount 186, such that the top surface 234 abuts the transverse bottom surface 189 of the grip mount 186. The bracket 232 defines an inner bore 244 configured to receive the post 226. The inner bore 244 extends through the bracket 244 past the top surface 234 and bottom surface 235 and through a spring support 249. The spring support 249 of the bracket 232 protrudes from the top surface 234 in a direction substantially parallel to the transverse axis T. In the depicted embodiment, the spring support 249 has a substantially cylindrical shape and can provide lateral support to spring 242 when mounted within the grip mount 186. The spring support 249 includes an inner shoulder 251 at an end adjacent to the top surface 234. The inner shoulder 251 changes the diameter of the inner bore 244. Accordingly, the diameter of the inner bore 244 is greater within the spring support 249 than between the top surface 234 and the bottom surface 235. The portion of the inner bore 244 within the spring support 249 can accommodate the spring 242 and the locking shaft 221, whereas the portion of the inner bore 244 between the top surface 234 and the bottom surface 235 can only accommodate the locking shaft 221. Aside from changing the diameter of the inner bore 244, the shoulder 251 defines a spring seat 247 suitable for supporting the spring 242. The release knob 231 is knob-shaped and defines an inner transverse bore 233 extending therethrough. Alternatively, the release knob 231 can be any shape suitable for any desired purpose. For instance, the release knob 231 can be configured and shaped so that it can be easily gripped by a human hand. The release knob 231 as illustrated can also include grooves 241 for improving the ability to grip the release knob 231. Alternatively, the release knob 231 can be devoid of grooves 241 or other features that enhance the ability to grip the release knob 231. When the inner bores 233 and 244 are aligned, the post 226 can be passed through them. The release knob 231 defines a second aperture 243 extending laterally therethrough that is aligned with the first aperture 239 when the post 226 is disposed in the bore 233. The locking mechanism 220 further includes a fastener 245, such as a pin, that is inserted through the aligned first and second apertures 239 and 243 to couple the release knob 231 to the locking shaft 221. The bracket 232 is disposed between the release knob 231 and the locking shaft 221, and defines a spring seat 247, such that the spring 242 extends between the spring seat 247 of the bracket 232 and the lower surface 229 of the collar 227 while the spring support 249 provides lateral support to the spring 242 Thus, the spring 242 provides a spring force that biases the locking shaft 221 upward toward the actuator 13.

During operation, the spring 242 biases the locking shaft 221 transversely up such that the engagement wall 240 is disposed in the recess 28 of the actuator 13. Interference between the locking shaft 221 and the actuator 13 prevents the spring 201 from biasing the actuator 13, and thus primary shaft 152, longitudinally rearward (see also FIG. 4). A downwardly directed force F3 can be applied to the release knob 231, which causes the locking shaft 221 to translate transversely down against the biasing force of the spring 242 until the key 230 is removed from the recess 28 and is thus out of interference with inner bore 184 of the housing body 181. Once the locking shaft 221 is out of interference with the actuator 13, the spring 201 biases the actuator 13 and the primary shaft 152 longitudinally rearward. The spring 201 is completely decompressed while the actuator 13 is disposed in the surgical instrument housing 11, and interference between the biasing member 60 and the actuator 13 prevents the actuator 13 and the primary shaft 152 from being completely removed from the surgical instrument housing 11. Once the force F3 is removed, the spring 242 biases the locking shaft 221 toward the primary shaft 152 until the engagement wall 240 abuts the elongate shaft 26 of the actuator 13.

Figure 11A:
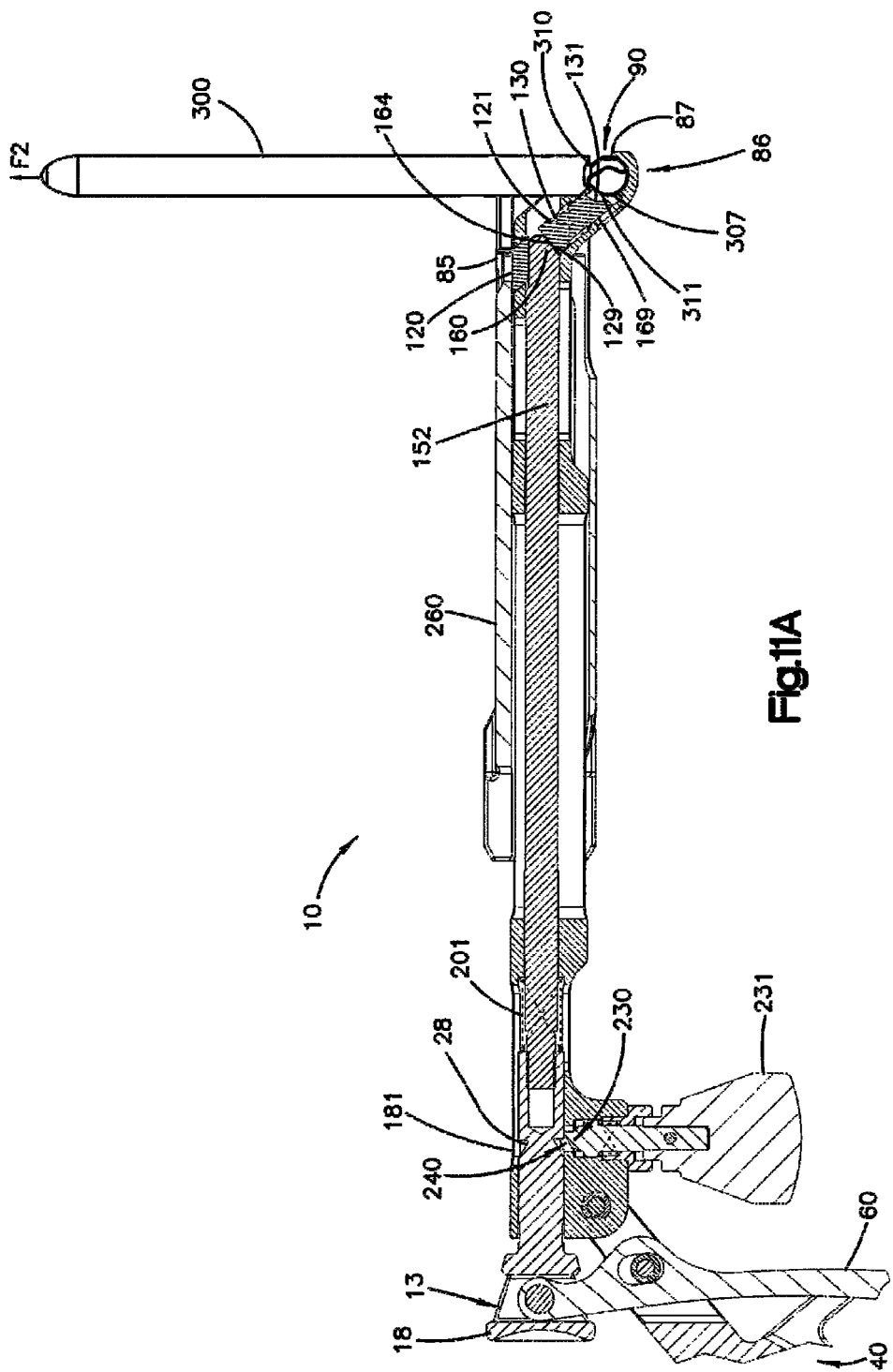
FIG. 11A is a sectional side elevation view of the surgical instrument as illustrated in 10A, taken along line 11A-11A, the surgical instrument being shown in a first configuration.
Figure 13B:
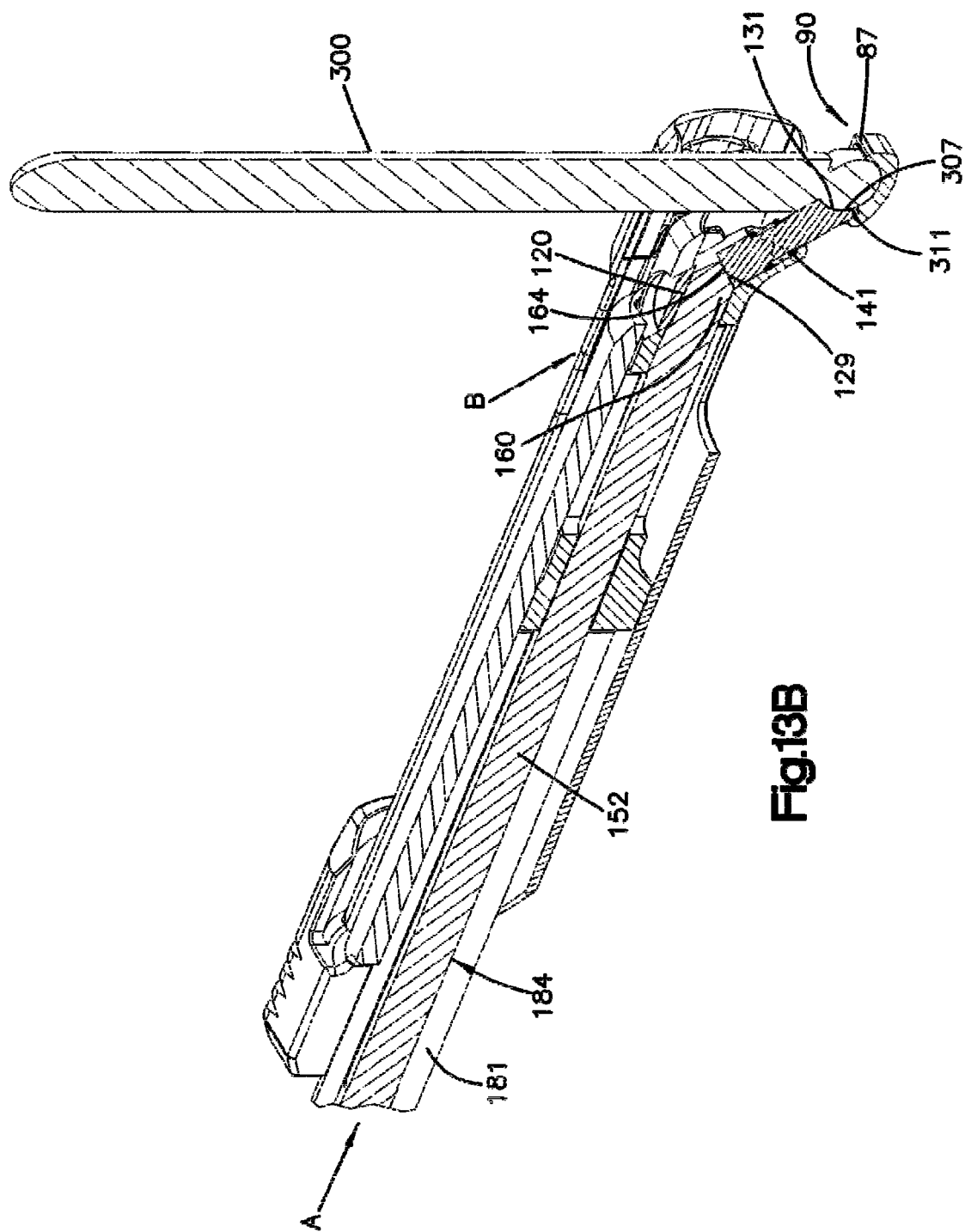
FIG. 13B is an enlarged cross-sectional perspective view of the distal portion of the surgical instrument as illustrated in FIG. 13A, but showing the surgical instrument in a second configuration.

Referring to FIGS. 11A-C and 13A-13C, the surgical instrument 10 is shown in three configurations that occur during the normal operation of the surgical instrument 10. Referring first to FIGS. 11A and 13A, the surgical instrument 10 is shown in a first configuration representing a steady state with no external forces being applied to the surgical instrument 10. In the first configuration, the actuator 13 is disengaged with the plug 18 such that the recess 28 is disposed proximal of the key 230, and the engagement wall 240 is not disposed in the recess 28. Also in the first configuration, the curved engagement surface 164 on the tips 160 of the primary shaft 152 are disposed proximal of the motion inhibitor 120; thus, the primary shaft 152 does not urge the engagement surface 129 of the motion inhibitor 120 toward the engagement tip 86. In other words, the primary shaft 152 does not engage or contact the motion inhibitor 120 when the surgical instrument 10 is in the first configuration. The spinal fixation rod 300 is disposed within the pocket 90 in the first transverse orientation. In the first configuration, the brake surface 131 of the motion inhibitor 120 is spaced apart from the curved top brake surface 311 of the brake 307, such that the spinal fixation rod 300 is free to rotate within the pocket 90 between the first orientation (FIG. 8A) and the second orientation (FIG. 8B) and the spinal fixation rod 300 can be removed from the pocket 90 with the application of the force F2 applied to the spinal fixation rod 300 in the direction of the arrow when the spinal fixation rod is in the first orientation. As stated above, if the spinal fixation rod 300 is in any orientation other than the first orientation illustrated in FIGS. 11A and 13A, applying force to the spinal fixation rod 300 will not result in its release from the pocket 90. In the first configuration, the spinal fixation rod 300 can be inserted into the pocket 90.

Figure 11B:
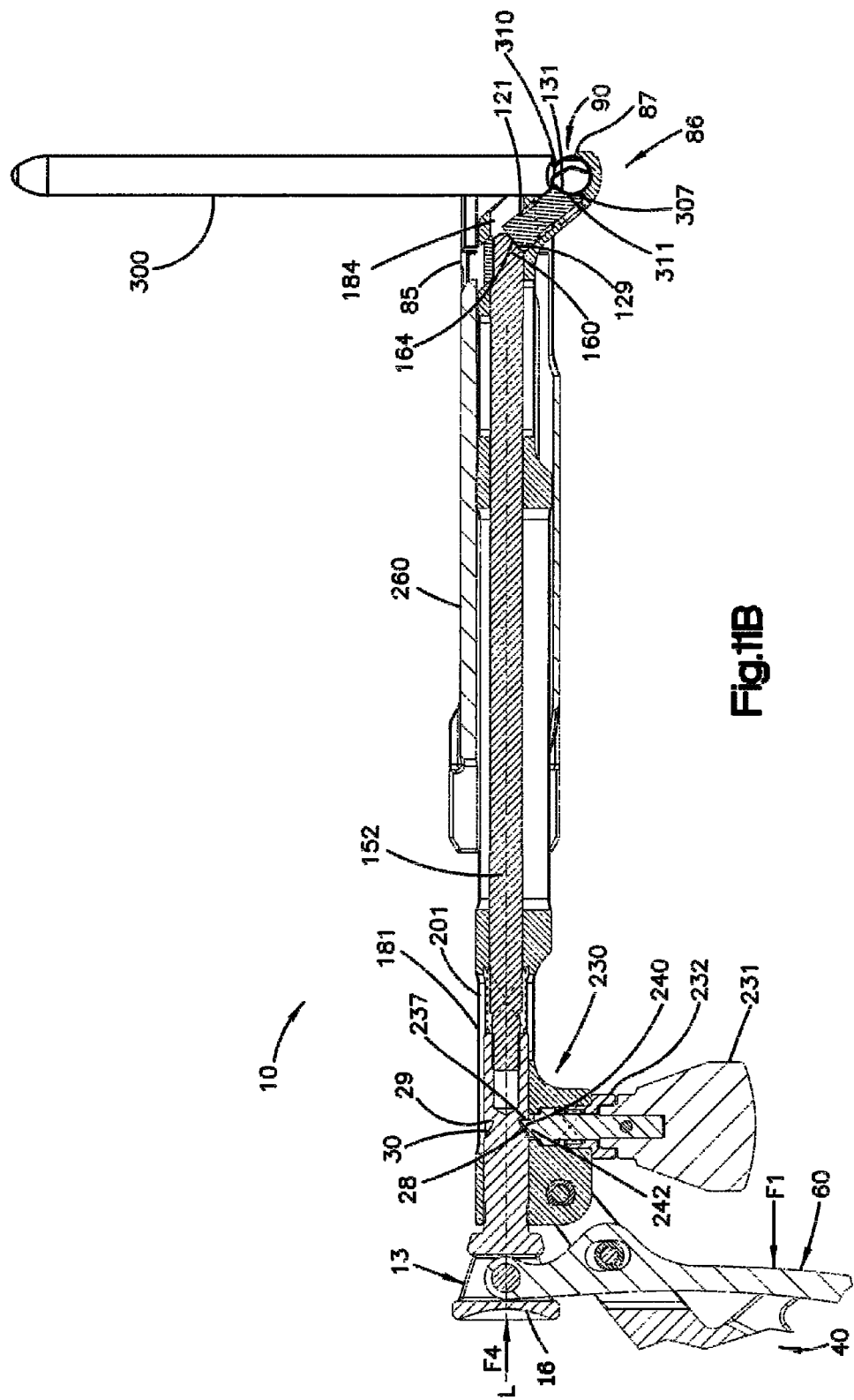
FIG. 11B is a cross-sectional view of the surgical instrument as illustrated in 11A, but showing the surgical instrument in a second configuration.

Referring to FIGS. 11B and 13B, the surgical instrument 10 can be moved from the first configuration to the second configuration by actuating the actuator 13. To do so, a force F4 is applied to the actuator 13 either via the biasing member 60 or directly to the biasing surface 16. To apply a longitudinally forward force F4 indirectly through the biasing member 60, the user may apply a force F1 to the biasing member 60 to move the biasing member 60 toward the grip 40. As the biasing member 60 moves toward the grip 40, the first upper proximal end 62 (FIG. 3) of the biasing member 60 applies a longitudinally forward force F4 to the actuator 13. The application of the force F4 urges the actuator 13 and the connected primary shaft 152 in a longitudinally distal direction (as indicated by arrow A in FIG. 13B) further into the inner bore 184 of the housing body 181 until the recess 28 is aligned with the key 230. When the recess 28 and key 230 are aligned, the spring 242 urges the key 230 into the inner bore 184 until the engagement wall 240 is inserted into the recess 28. In this second configuration, the longitudinally proximal translation of the actuator 13 and the primary shaft 152 away from the engagement assembly 80 is prevented by the interference between the flat transverse wall 237 of the key 230 and the side wall 29.

As the primary shaft 152 translates longitudinally forward to the second configuration in the direction indicated by arrow A, the curved engagement surfaces 164 on the tips 160 of the primary shaft 152 (FIG. 4) contact the engagement surface 129 of the motion inhibitor 120 (FIG. 6B) and urge the motion inhibitor 120 toward the engagement tip 86 within the inner bore 85 (in the direction as indicated by arrow B). Once the surgical instrument 10 is in the second configuration, the brake surface 131 of the motion inhibitor 120 has entered the pocket 90 and is either slightly spaced from the curved top surface 311 of the brake 307, or abuts the curved top surface 311 but not under pressure that is substantial enough to cause the brake surface 131 to prevent, or at least inhibit, the spinal fixation rod 300 from pivoting in the pocket 90. Therefore, when the surgical instrument 10 is in the second configuration, the spinal fixation rod 300 is able to pivot in the pocket 90.

Furthermore, when the surgical instrument 10 is in the second configuration, the spinal fixation rod 300 is unable to be removed from the pocket 90 regardless of its angular orientation. In particular, the previous direction of removal of the spinal fixation rod 300 is now blocked by the interference between the brake surface 131 and the curved top surface 311 of the brake 307. In this regard, the brake surface 131 and the lip 87 define a circumferential distance therebetween of greater than 180° such that the brake 307 (FIGS. 7A-7B) is captured between the brake surface 131 and the lip 87. Thus, the brake surface 131 and the lip 87 provide a lock that precludes removal of the spinal fixation rod 300 from the surgical instrument 10 in the second configuration.

As described with reference to FIG. 4, it should be appreciated that the position of the brake surface 131 of the auxiliary shaft 121 relative to the brake surface 311 of the spinal fixation rod 300 in the second configuration can be tuned by rotating the shaft 152 and/or the actuator 13 relative to each other, which causes the shaft 152 to advance forward or retract rearward as the threads 156 and 25 engage. As the shaft 152 advances forward, the curved engagement surface 164 is brought into further contact with the engagement surface 129 of the of the auxiliary shaft 121 and urges the auxiliary shaft 121, and thus, the brake surface 131, further toward the curved top surface 311. Conversely, as the shaft 152 is retracted rearward, the curved engagement surface 164 translates away from the engagement surface 129 of the of the auxiliary shaft 121, such that the force of the spring 141 (see FIGS. 6A-B) urges the auxiliary shaft 121, and thus the brake surface 131, away from the brake surface 311. Thus, the threaded connection between the actuator 13 and the shaft 152 can be adjusted such that the brake surface 131 does not prevent the spinal fixation rod 300 from pivoting in the pocket 90, but provides a lock in combination with the lip 87 that prevents the spinal fixation rod 300 from being removed from the pocket 90.

Figure 11C:
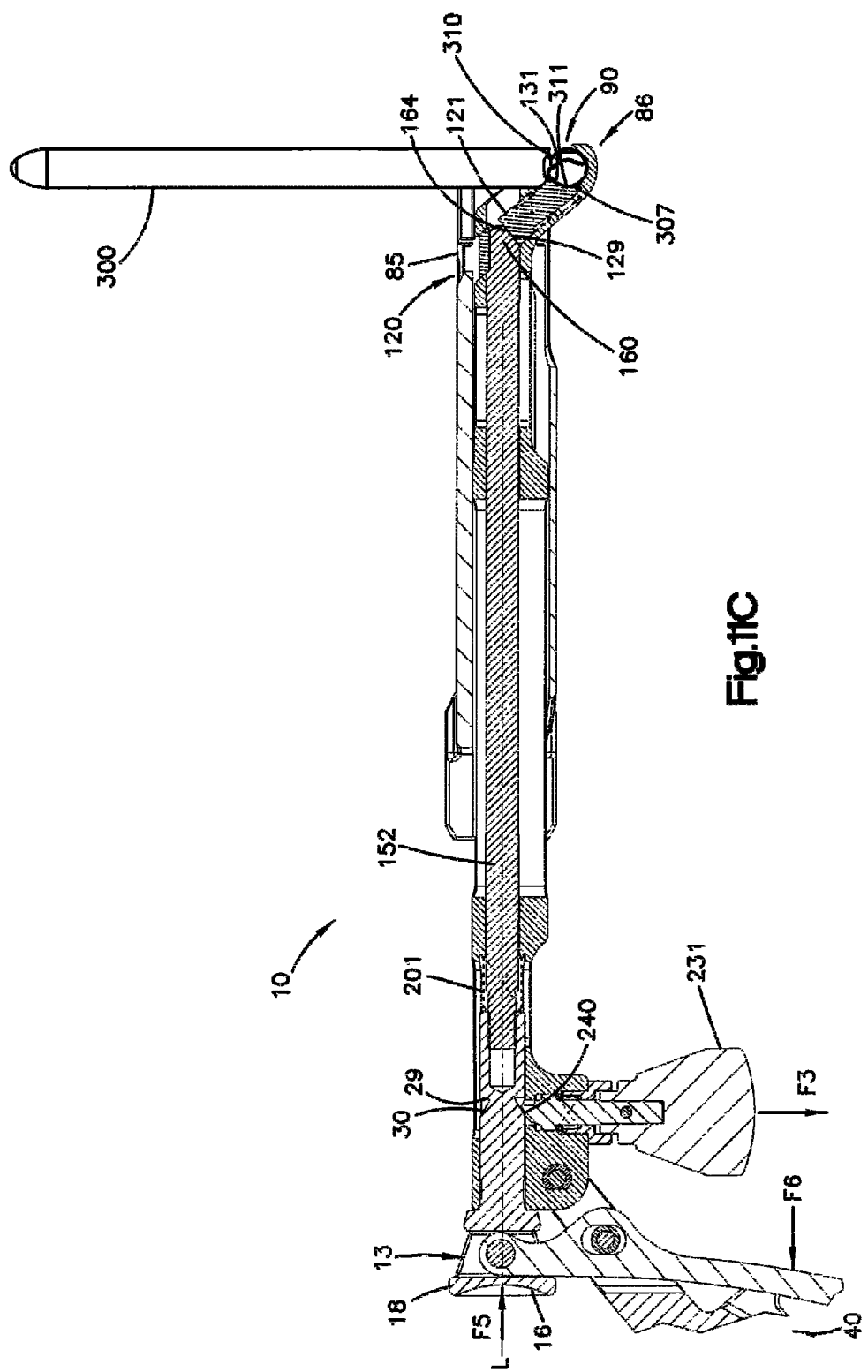
FIG. 11C is a cross-sectional view of the surgical instrument as illustrated in 11A, but showing the surgical instrument in a third configuration.

Referring now to FIGS. 11C and 13C, the surgical instrument 10 is shown in the third configuration. To reach the third configuration from the second configuration, a user once again actuates the actuator 13. To do so, a further longitudinally forward force F5 is applied to the actuator 13 either via the biasing member 60 or directly to the actuator 13, so that the actuator 13 and the primary shaft 152 translate further longitudinally forward. As discussed above, the user may apply longitudinally forward force F5 to the actuator 13 by applying a force F6 to the biasing member 60 to urge its first upper proximal end 62 (FIG. 3) forward. In turn, the first upper proximal end 62 of the biasing member 60 applies the longitudinally forward force F5 to the actuator 13. Further forward translation of the primary shaft 152 in the direction indicated by arrow C causes the engagement surface 164 to urge the complementary engagement surface 129 of the motion inhibitor 120 distally in the direction indicated by arrow D toward the curved top surface 311, which in turn causes the brake surface 131 to exert sufficient pressure against the curved top surface 311 to prevent, or at least inhibit, the spinal fixation rod 300 from pivoting in the pocket 90. In particular, the pressure between the brake surface 131 and the curved top surface 311 creates a frictional force that resists an externally applied pivotal force to the spinal fixation rod 300, thereby precluding, or at least hindering, pivotal movement of the spinal fixation rod 300 relative to the surgical instrument 10. In the third configuration, the brake surface 131, in combination with the lip 87, continues to provide a lock that prevents the spinal fixation rod 300 from being removed from the pocket 90 regardless of the angular orientation of the spinal fixation rod.

The surgical instrument 10 can be returned from the third configuration to the second configuration by removing the force F6 from the biasing member 60 and/or the force F5 from the actuator 13, which causes the brake surface 131 to be removed from braking engagement with the brake surface 311. The surgical instrument 10 can be returned to the first configuration by applying the downward force F3 onto the release knob 231, which causes the actuator assembly 12 to assume a disengaged configuration. In particular, the engagement wall 240 is removed from the recess 28 of the actuator 13, such that the spring 201 (FIG. 5B) biases the actuator 13 rearward, thereby causing the primary shaft 152 to translate rearward away from the auxiliary shaft 121. Removal of interference between the primary shaft 152 and the auxiliary shaft 121 allows the biasing force provided by the spring 141 (FIG. 6A) to translate the auxiliary shaft, and thus the brake surface 131, away from brake surface 311 of the spinal fixation rod 300.

Figure 12:
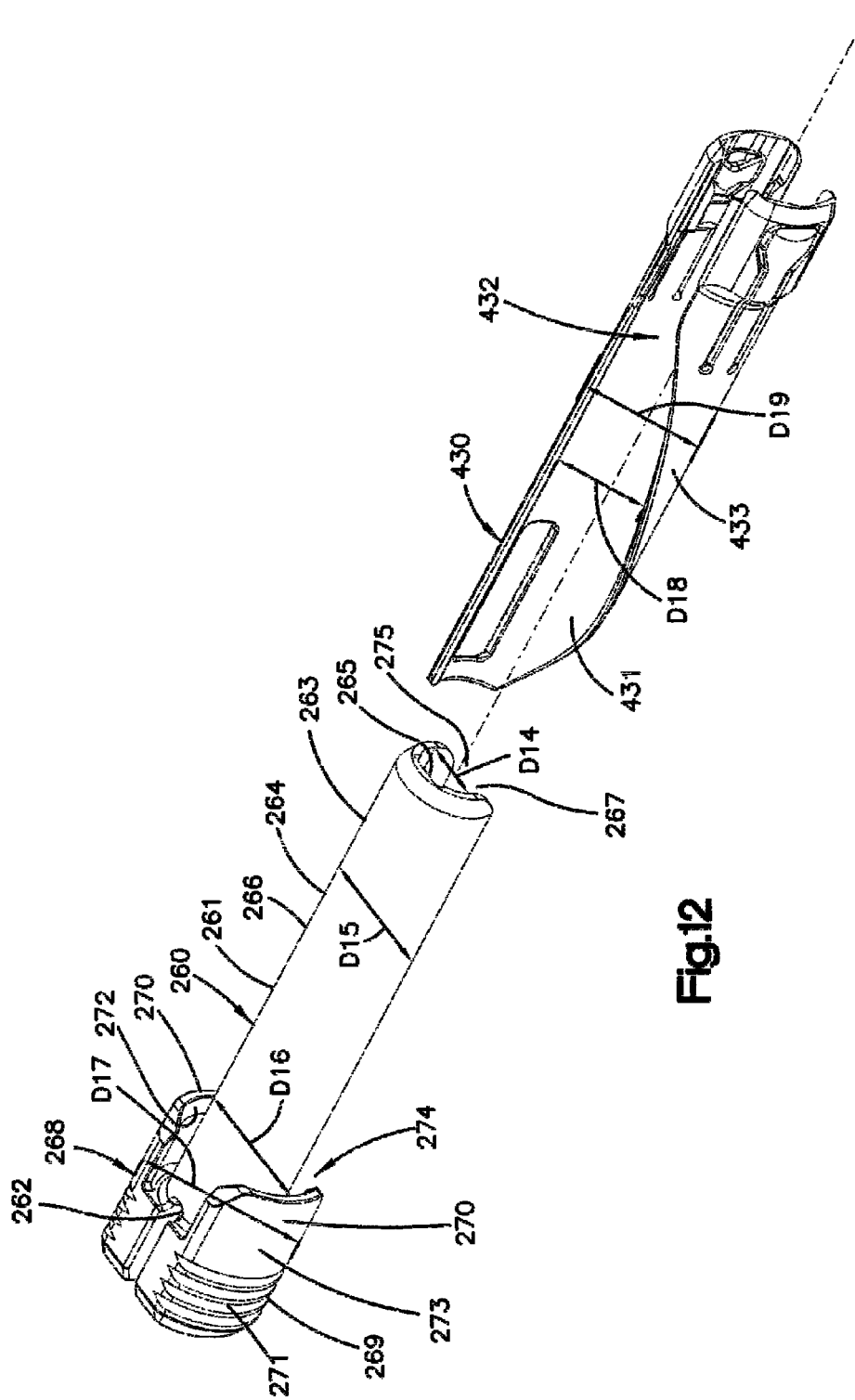
FIG. 12 is a perspective view of a centering sleeve and a tissue retractor.

Referring now to FIG. 12, the surgical system 8 further includes a centering sleeve 260 that can be removably attached to the surgical instrument 10. The centering sleeve 260 includes a substantially tubular centering sleeve body 261 that defines a first proximal end 262, an opposed second distal end 263 and an elongate portion 264 extending from the proximal end 262 to the distal end 263. The elongate portion 264 presents an inner surface 265 that defines an inner diameter D14 and an outer surface 266 that defines an outer diameter D15. The inner surface 265 of the elongate portion 264 also defines a channel 267, which extends through the first end 262 and the second end 263. The channel 267 has an open end 275 configured to receive the outer surface 185 of the housing body 181 (see FIG. 5A), such that the centering sleeve body 261 fits over the housing body 181. The channel 267 is oblong and sized to snugly receive the outer surface 185 of the housing body 181, which can also be oblong. Therefore, the centering sleeve 260 fits onto the housing body 181 in a predetermined orientation.

With continuing reference to FIG. 12, the centering sleeve 260 includes a raised portion 268 that projects out from the proximal end 262 of the centering sleeve body 261. The raised portion 268 defines a grip 269 that can include texture such as grooves 271 and is sized and shaped to be comfortably gripped and manipulated by a human hand. The raised portion 268 further includes one or more flanges 270 that project distally from the grip 269. The flange 270 presents an inner surface 272 that defines an inner diameter D16 and an outer surface 273 defining an outer diameter D17. The inner surface 272 is elongate parallel to the opposing outer surface 266 of the elongate portion 264. A gap 274 is defined between the inner diameter D16 and the outer diameter D15. The gap 274 is sized to slidably receive a tissue retractor 430 of a vertebral implant 400 (See FIG. 2).

Referring still to FIG. 12, the retractor 430 is a substantially tubular member and presents an inner surface 431 that defines a channel 432 and an inner diameter D18, and an outer surface 433 defining an outer diameter D19. The inner diameter D18 is greater than the outer diameter D15 such that the channel 432 can be fit over and slidably engage with the outer surface 266. The outer diameter D19 of the retractor 430 is less than inner diameter D16 of the flange 270, such that the retractor 430 is slidably receivable within the gap 274. The retractor 430 is shaped such that it is received within the gap 274 only in a predetermined orientation.

The following is one embodiment of a method of use of the surgical instrument 10. Referring to FIGS. 1 and 2, a vertebral implant 400 is selected, which includes a plurality of pedicle screws 400, each including a bone anchor 410 and an anchor seat 420. A retractor 430 can extend out from one or more of the pedicle screws 400. The retractor 430 is releasably attached to the anchor seat 420. The bone anchor 410 is seated within the anchor seat 420 and the bone anchor 410 is then secured to a vertebra (or other bone or surface) through drilling or screwing. A spinal fixation rod 300 is selected from a plurality of different spinal fixation rods 300 of different sizes and shapes. The selected spinal fixation rod 300 is engaged with the engagement assembly 80 of the surgical instrument housing 11 that is in the first configuration. A force F1 is applied to the biasing member 60, which causes the transfer assembly 150 to translate within the surgical instrument housing 11 until the surgical instrument 10 is in the second configuration. The locking mechanism 220 engages the actuator assembly 12, thereby retaining the surgical instrument 10 in the second configuration.

While in the second configuration, the engagement assembly 80 prevents the removal of the spinal fixation rod 300 from the surgical instrument housing 11. The spinal fixation rod 300 is pivotable with respect to the surgical instrument housing 11 to a desired angular orientation. An additional force can be applied to the biasing member 60, thereby urging the actuator 13 and the actuation member further into the housing body 181 and thus moving the surgical instrument housing 11 into the third configuration, whereby the spinal fixation rod 300 is not only unable to be removed from the engagement assembly 80 via the application of a force to the spinal fixation rod 300, but the spinal fixation rod 300 is also prevented from freely pivoting within the engagement assembly 80 due to the friction created through contacting members of the surgical instrument 10 and the spinal fixation rod 300.

A user can advance the spinal fixation rod 300 into the retractor 430 by manipulating the grip 40. Next, the centering sleeve 260 is placed onto the housing body 181 and then is slid along the longitudinal axis L toward the retractor 430 until the retractor 430 is secured within the gap 274. When positioned within the retractor 430, the centering sleeve 260 centers the surgical instrument 10 with respect to the tissue retractor 430 so that the spinal fixation rod 300 can be implanted at a predetermined location relative to the vertebral implant 400. Once the centering sleeve 260 has secured the housing body 181 to the retractor 430, the spinal fixation rod 300 is properly positioned within the retractor 430. The properly positioned spinal fixation rod 300 is then secured to the anchor seat 420, for instance by securing a locking cap onto the anchor seat 420. Alternatively, the surgical system 8 can be used without the centering sleeve 260. In the absence of a centering sleeve 260, the projection 195 (see FIGS. 5A and 5B) of the surgical instrument housing 11 can act as a centering spacer when the surgical instrument housing is placed within the tissue retractor 430 so as to center the surgical instrument 10 relative to the tissue retractor 430 in order to implant the spinal fixation rod 300 at a predetermined location relative to the vertebral implant 400. Vertebral implants such as the vertebral implant 400 are disclosed in PCT Patent Application Serial No. PCT/US2008/070670, having an international filing date of Jul. 21, 2008, the entire disclosure of which is hereby incorporated by reference as if set forth in its entirety herein. To disengage the surgical instrument 10 from the spinal fixation rod 300, the release knob 231 of the locking mechanism 220 is actuated to remove the locking shaft 221 from the actuator assembly 12 so as to disengage the actuator 13.

It should be further appreciated that a surgical kit can be provided that can include any or all of the above-described components, either as individual components or as a plurality of differently sized components. For instance, the kit can include the surgical instrument 10 as described above and a plurality of spinal fixation rods 300 that can have different sizes or shapes or alternatively be uniform.

The embodiments described in connection with the illustrated embodiments have been presented by way of illustration, and the present invention is therefore not intended to be limited to the disclosed embodiments. Furthermore, the structure and features of each the embodiments described above can be applied to the other embodiments described herein, unless otherwise indicated. For instance, while various components have been described as defining diameters, it should be appreciated that the described structure need not be circular, and thus the diameters can instead be defined by any suitably shaped cross section as desired. Accordingly, those skilled in the art will realize that the invention is intended to encompass all modifications and alternative arrangements included within the spirit and scope of the invention, for instance as set forth by the appended claims.

What is claimed:

1. A surgical instrument for implanting a spinal fixation rod, comprising:

an engagement assembly including a motion inhibitor configured to releasably engage the spinal fixation rod, a first engagement wall and a second engagement wall spaced from the first engagement wall so as to define a rod receiving gap that extends between the first and second engagement walls, the rod receiving gap configured and sized to receive a portion of the spinal fixation rod and to permit the spinal fixation rod to pivot therein between a plurality of spinal rod orientations, the engagement assembly further including at least one retaining wall and an engagement surface carried by the first engagement wall, the at least one retaining wall being spaced from the engagement surface so as to define a retaining gap that extends between the at least one retaining wall and the engagement surface, the retaining gap being shaped to match and receive a complementary surface of the portion of the spinal fixation rod such that the spinal fixation rod can be removed from the engagement assembly only when the spinal fixation rod is in one of the plurality of rod orientations;

a transfer assembly comprising a shaft operably coupled to the motion inhibitor; and an actuator operably coupled to the shaft so as to translate the shaft upon actuation of the actuator; and wherein movement of the shaft causes at least one of the first and second engagement walls to move toward the other of the first and second engagement walls between a first position in which the rod receiving gap has a first size and a second position in which the rod receiving gap has a second size, the second size being less than the first size.

2. The surgical instrument according to claim 1, wherein the motion inhibitor is movable upon translation of the shaft to a third position in which the rod receiving gap has a third size, the third size being less than the second size.

3. The surgical instrument according to claim 1, wherein the engagement assembly defines an ejection port in communication with the rod receiving gap, the ejection port facing a direction substantially perpendicular to a longitudinal axis defined along a length of the surgical instrument.

4. The surgical instrument according to claim 3, wherein the lip extends along a transverse direction that is substantially perpendicular to the longitudinal axis.

5. The surgical instrument according to claim 4, wherein the lip, and the at least one retaining wall at least partially define an engagement pocket, and the spinal fixation rod can be removed from the engagement pocket when the spinal fixation rod is substantially perpendicular to the longitudinal axis.

6. The surgical instrument according to claim 1, wherein the motion inhibitor comprises an auxiliary shaft having first and second ends, the auxiliary shaft comprising a curved brake surface at the second end thereof, the curved brake surface being configured to contact the spinal fixation rod.

7. The surgical instrument according to claim 6, wherein the curved brake surface has a substantially concave configuration.

8. The surgical instrument according to claim 6, wherein the curved brake surface of the motion inhibitor is configured to receive a curve brake surface of the spinal fixation rod.

9. The surgical instrument according to claim 1, further comprising a surgical instrument body defining a longitudinal axis and connected to the actuator and the engagement assembly.

10. The surgical instrument according to claim 9, wherein the surgical instrument body defines an inner bore extending along the longitudinal axis, the inner bore being configured and dimensioned to slidably receive the shaft.

11. The surgical instrument according to claim 10, wherein the engagement assembly defines an engagement pocket and a transverse bore configured and dimensioned to slidably receive the motion inhibitor, the transverse bore being in communication with the inner bore.

12. The surgical instrument according to claim 11, wherein the engagement assembly further comprises a biasing member disposed within the transverse bore and surrounding the motion inhibitor, the biasing member being configured to bias the motion inhibitor away from the engagement pocket.

13. The surgical instrument according to claim 11, wherein the lip is configured as a stop, limiting the pivotal motion of the spinal fixation rod when disposed in the engagement pocket.

14. The surgical instrument according to claim 1, wherein the motion inhibitor includes the second engagement wall at a distal end thereof.

15. A system for implanting a spinal fixation rod, comprising:
 a spinal fixation rod having a first end and a second end opposed to the first end; and
 a surgical instrument comprising:
  an engagement assembly including a motion inhibitor configured to releasably engage the spinal fixation rod, a first engagement wall, and a second engagement wall carried by the motion inhibitor and spaced from the first engagement wall so as to define a rod receiving gap that extends between the first and second engagement walls, the rod receiving gap configured and sized to receive the first end of the spinal fixation rod and to permit the spinal fixation rod to pivot therein between a plurality of rod orientations,
  the engagement assembly further including at least one retaining wall and an engagement surface carried by the first engagement wall, the at least one retaining wall being spaced from the first engagement wall and the engagement surface so as to define a retaining gap, the retaining gap being shaped to match and receive a complementary surface of the first end of the spinal fixation rod such that the spinal fixation rod can be removed from the engagement assembly only when the spinal fixation rod is in one of the plurality of rod orientations,
  a transfer assembly comprising a shaft operably coupled to the motion inhibitor; and
  an actuator operably coupled to the shaft so as to translate the shaft upon actuation of the actuator; and
 wherein movement of the shaft causes the second engagement wall to move along the at least one retaining wall toward the first engagement wall between a first position in which the rod receiving gap has a first size and a second position in which the rod receiving gap has a second size, the second size being less than the first size.

16. The system according to claim 15, wherein the motion inhibitor is movable upon translation of the shaft to a third position in which the rod receiving gap has a third size, the third size being less than the second size.

17. The system according to claim 15, wherein the engagement assembly defines an ejection port in communication with the rod receiving gap, the ejection port facing a direction substantially perpendicular to a longitudinal axis defined along a length of the surgical instrument.

18. The system according to claim 17, wherein the engagement assembly includes a lip that extends along direction that is substantially perpendicular to the longitudinal axis.

19. The system according to claim 18, wherein the at least one retaining wall, the first engagement wall and the lip define an engagement pocket, and the engagement pocket is contoured and sized to allow removal of the spinal fixation rod therefrom only when the spinal fixation rod axis is substantially perpendicular to the longitudinal axis of the surgical instrument.

20. The system according to claim 15, wherein the motion inhibitor comprises an auxiliary shaft having first and second ends, the auxiliary shaft comprising a curved brake surface at the second end thereof, the curved brake surface being configured to contact the spinal fixation rod.

21. The system according to claim 20, wherein the curved brake surface has a substantially concave configuration.

22. The system according to claim 20, wherein the curved brake surface of the motion inhibitor is configured to receive a curved brake surface of the spinal fixation rod.

23. The system according to claim 15, further comprising a surgical instrument body defining a longitudinal axis and connected to the actuator and the engagement assembly.

24. The system according to claim 23, wherein the surgical instrument body defines an inner bore extending along the longitudinal axis, the inner bore being configured and dimensioned to slidably receive the shaft.

25. The system according to claim 24, wherein the engagement assembly defines an engagement pocket and a transverse bore configured and dimensioned to slidably receive the motion inhibitor, the transverse bore being in communication with the inner bore.

26. The system according to claim 25, wherein the engagement assembly further comprises a biasing member disposed within the transverse bore and surrounding the motion inhibitor, the biasing member being configured to bias the motion inhibitor away from the engagement pocket.

27. The system according to claim 18, wherein the a lip that acts as stop that is configured to limit the pivotal motion of the spinal fixation rod disposed in the engagement assembly.

28. The system according to claim 15, wherein the motion inhibitor includes the second engagement wall at a distal end thereof.

* * * * *